(12) United States Patent
Nan et al.

(10) Patent No.: US 7,683,073 B2
(45) Date of Patent: Mar. 23, 2010

(54) ISOQUINOLINE-1,3,4-TRIONE COMPOUNDS, THE SYNTHETIC METHOD AND THE USE THEREOF

(75) Inventors: Fajun Nan, Shanghai (CN); Jia Li, Shanghai (CN); Yihua Chen, Shanghai (CN); Yahui Zhang, Shanghai (CN); Min Gu, Shanghai (CN); Huajie Zhang, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 1023 days.

(21) Appl. No.: 11/301,638

(22) Filed: Dec. 13, 2005

(65) Prior Publication Data

US 2006/0135557 A1 Jun. 22, 2006

(51) Int. Cl.
*C07D 217/22* (2006.01)
*A61K 31/47* (2006.01)

(52) U.S. Cl. ............. 514/300; 514/309; 546/113; 546/142

(58) Field of Classification Search ............... None
See application file for complete search history.

(56) References Cited

FOREIGN PATENT DOCUMENTS

EP        1193257         4/2002

OTHER PUBLICATIONS

Ling et al, Tetrahedron, 1999, vol. 55, No. 30, pp. 9186-9204.*
Mishima et al., Heterocycles, (1977), vol. 6 (9-10), pp. 1652-1657.*

Jean Tirouflet, et al. "Synthesis and Physicochemical Properties of Substituted Phthalonimides," Chemical Abstracts Service, Columbus, Ohio, p. 1, 1958.
Rene Dabard, "Condensation Products of Homophthalimides and Aromatic and Heterocyclic Aldehydes," Chemical Abstracts Service, Columbus, Ohio, p. 1, 1957.
Tetsuya Kita, et al. "Thymidine Phosphorylase Inhibitors with a Homophthalimide Skeleton," *Biological & Pharmaceutical Bulletin*, vol. 24, No. 7, pp. 860-862, 2001.
Glynn Mitchell, et al. "1,3,4(2H)-Isoquinolinetriones: Evaluation of Amino-Substituted Derivatives as Redox Mediator Herbicides," *Pest Management Science*, vol. 56, No. 2, pp. 120-126, 2000.
Ling Ke-Qing, et al. "On the Reactions of 1,3-Isoquinolinediones with Singlet Oxygen," *Tetrahedron*, vol. 55, No. 30, pp. 9185-9204, 1999.
Marco Mazza, et al. "Herbicidal Activity of 2-substituted 1,3,4-(2H)-isoquinolinetriones," *Farmaco*, vol. 54, No. 6, pp. 339-345, 1999; and American Chemical Society, Search Strategy (131:181047), 2002.
Ling Ke-Qing, et al. "Dye-Sensitized Photooxygenations of 1,3-Isoquinolinediones," *Tetrahedron Letters*, vol. 39, No. 16, pp. 2381-2384, 1999.
C. Pollers-Wieers, et al. "The Use of Isoquinolinetriones in the Synthesis of Benzo[c]phenanthridine Alkaloids," *Tetrahedron*, vol. 37, No. 24, pp. 4321-4326, 1981.
Jozef Vekemans, et al. "A New Pathway to 1,3,4(2H)-Isoquinolinetriones and Substituted Isoindolinones," *Tetrahedron*, vol. 36, No. 7, pp. 943-950, 1980.
N.P. Buu-Hoi, et al. "Phthalonimides (1,3,4-Trioxo-1,2,3,4-Tetrahydroisoquinolines) of Potential Biological Interest," *Journal of Heterocyclic Chemistry*, 5(4), pp. 545-547, 1968.

* cited by examiner

*Primary Examiner*—Zinna N Davis
(74) *Attorney, Agent, or Firm*—Baker & Hostetler LLP

(57) ABSTRACT

The invention relates to various substituted isoquinoline-1,3,4-trione, the synthetic method thereof and the use for treating neurodegenerative diseases, especially as the medicine for Alzheimer's disease, apoplexy and brain ischemic injuries.

9 Claims, 5 Drawing Sheets

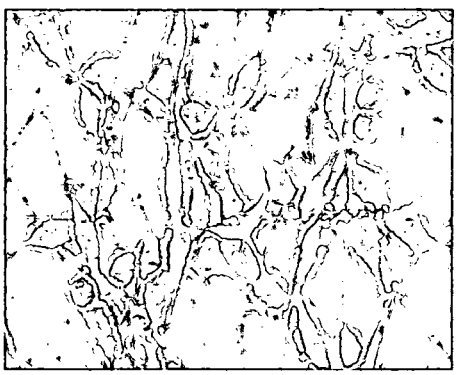
Fig.1. Morphology of PC12 cells in 1% dimethyl sulfoxide.
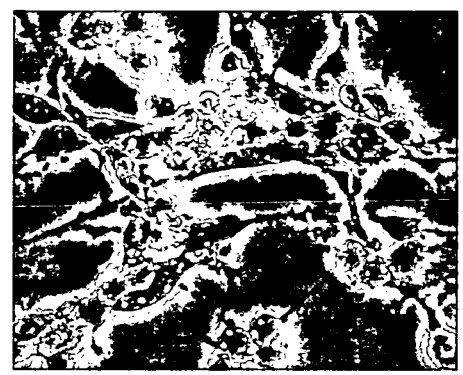
Fig.2. Morphology of PC12 cells in a mixture of 1% dimethyl sulfoxide and 20μM Aβ
Fig.3. Morphology of PC12 cells in 200nM Ac-DEVD-CHO.
Fig.4 is morphous of PC12 cells in a mixture of 200nM Ac-DEVD-CHO and 20μM Aβ
Fig.5. Morphology of PC12 cells in 28μM chen-1.
Fig.6. Morphology of PC12 cells in a mixture of 28μM chen-1 and 20μM Aβ

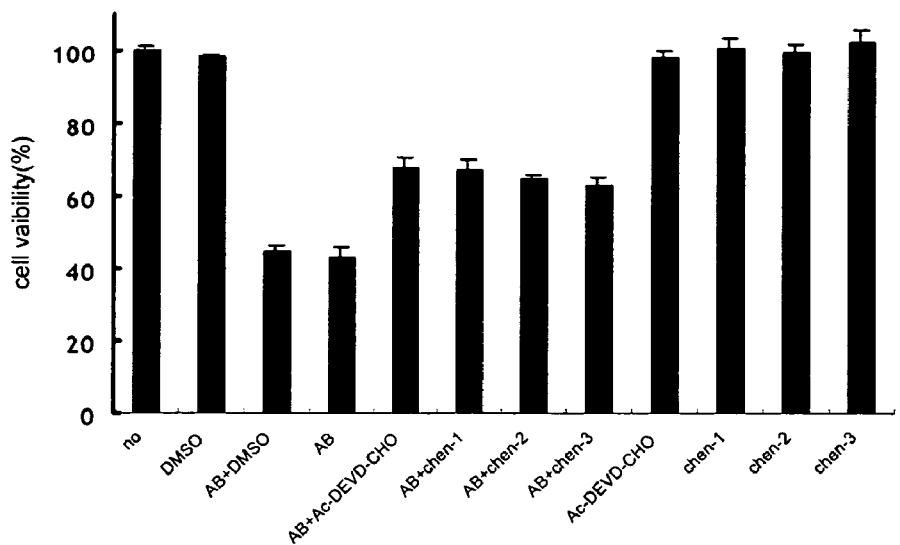
Fig.7. Effect of different Caspase-3 inhibitors on viability of apoptosis of PC12 induced by Aβ
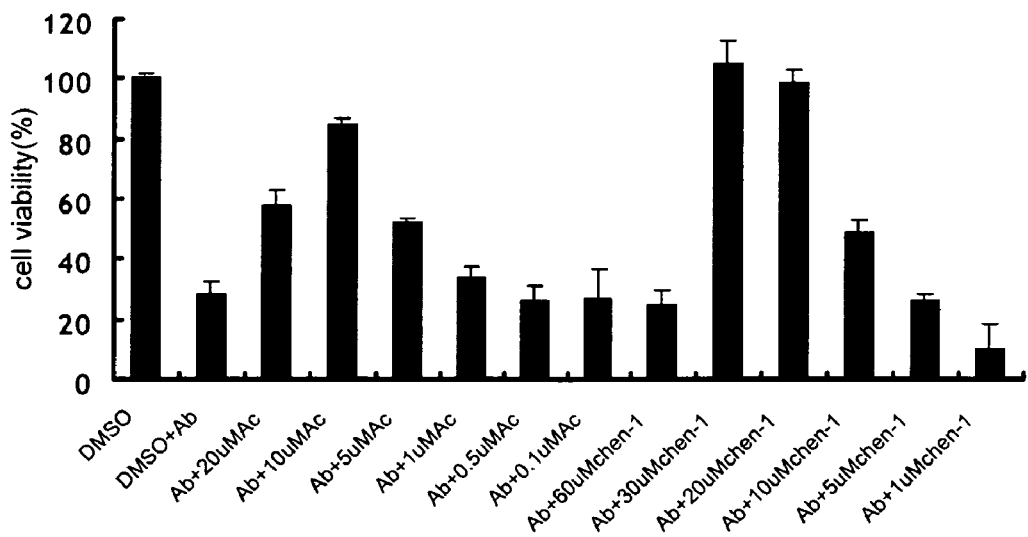
Fig.8. Effect of Caspase-3 inhibitors with different concentration on viability of apoptosis of PC12 induced by Aβ

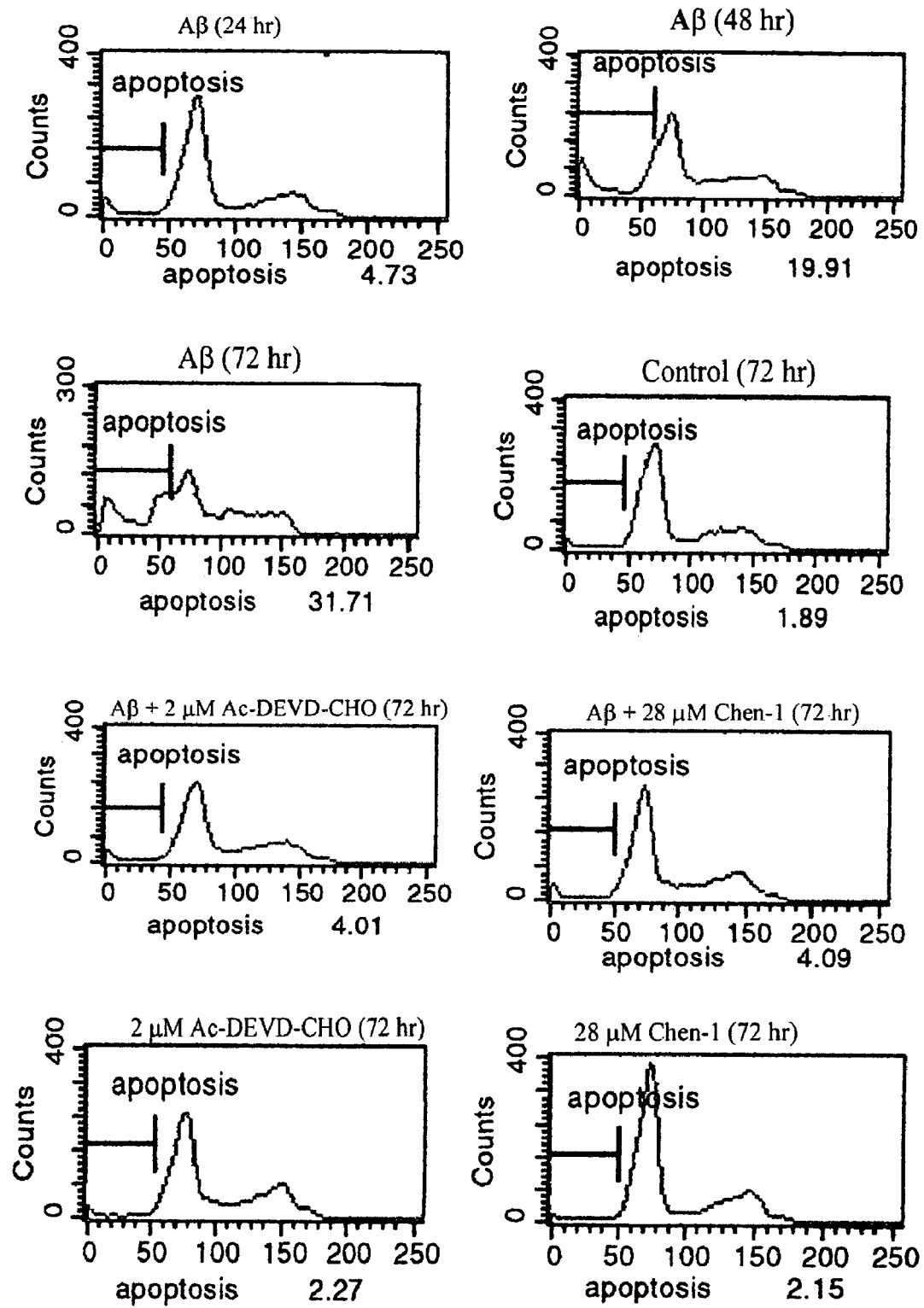
Fig.9 Results of flow cytometry of the effect on PC12 cells of Caspase-3 inhibitors and 20μM Aβ

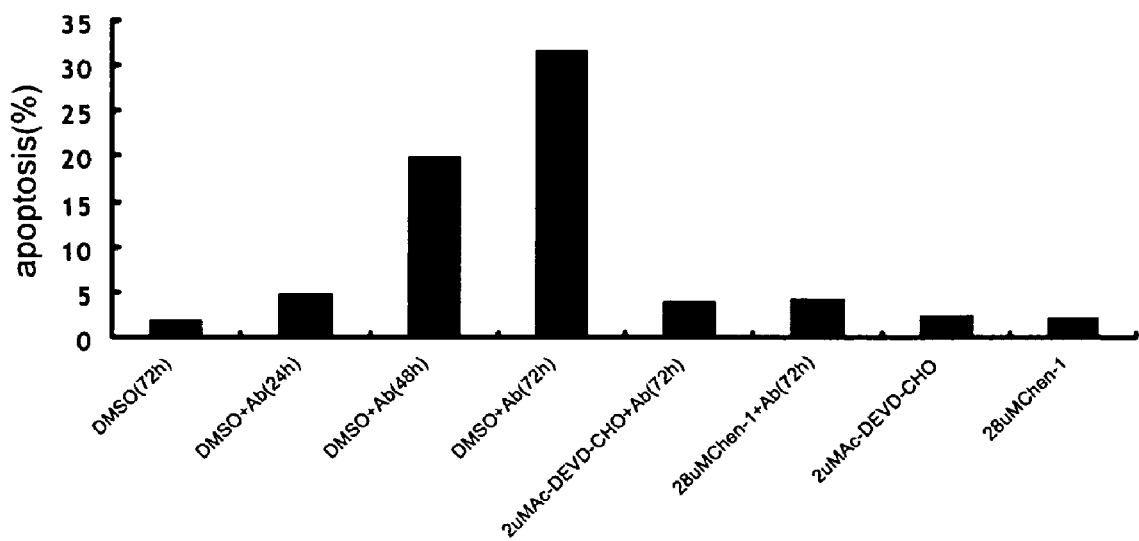
Fig.10 Effect of 20μM Aβ and Caspase-3 inhibitors on the percentage of apoptosis of PC12

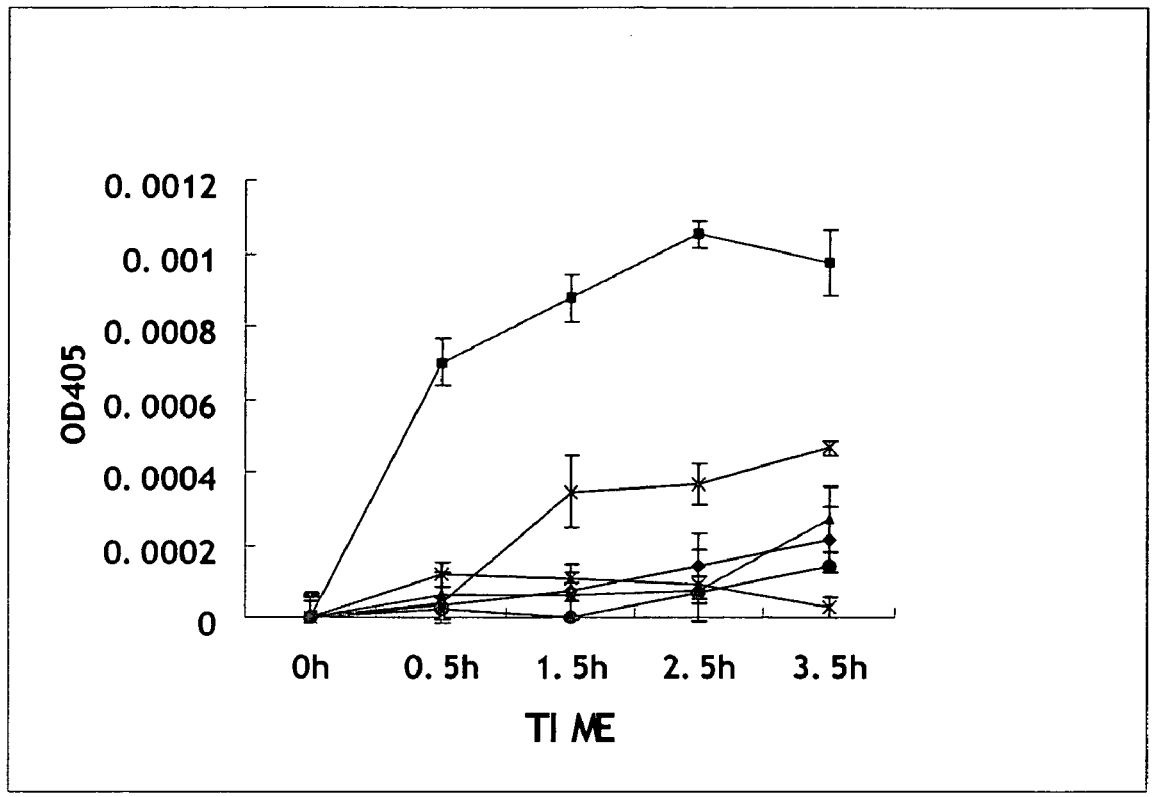
Fig.11 Activity of PC12 cells treated with 20μM Aβ and caspase-3 inhibitors for 10 hours, in which—□—represents 1% dimethyl sulfoxide ; —■—represents Aβ+ dimethyl sulfoxide ; —▲—represents Aβ+2μM Ac-DEVD-CHO ; —x—represents Aβ+28μM chen-1 ; —*—represents 2μM Ac-DEVD-CHO , —●—represents 28μM chen-1

ISOQUINOLINE-1,3,4-TRIONE COMPOUNDS, THE SYNTHETIC METHOD AND THE USE THEREOF

CLAIM OF PRIORITY

This claims priority under 35 U.S.C. §120 to International Patent Application Serial No. PCT/CN2004/000567 filed on May 31, 2004, which claims priority to People's Republic of China Patent Application Serial No. CN 03129250.X filed on Jun. 13, 2003 the teachings of both applications being incorporated herein by reference.

FIELD OF THE INVENTION

The invention relates to isoquinoline-1,3,4-trione compounds, the synthetic method and the use thereof. This kind of compounds can be used as caspase inhibitors and nerve protectors to treat various neurodegenerative diseases, especially Alzheimer's disease, apoplexy and ischemic brain injuries.

DESCRIPTION OF THE RELATED ART

The teachings of all of the references cited herein are incorporated herein in their entirety by reference.

Apoptosis is a spontaneous process of death of normal organism cells coming under a physiological and pathological stimulation, and has an important role in histodifferentiation, organ development, and maintenance of organism homeostasis for a multicellular organism. While new cells are generated, the senile and mutant cells are cleared out through the apoptosis mechanism to ensure organs and tissues develop and metabolize normally. Apoptosis also participates in some pathologic processes, such as cancer, autoimmune disease, viral infection and neurodegenerative diseases, etc. Due to its great importance, apoptosis has remained in organic evolution from simple multicellular organisms such as a wireworm to highly evolved mammals such as human.

Apoptotic cells have different morphologic changes than necrotic cells, and the most remarkable features include condensation of nuclear chromatin, breakage of chromosomal DNA, and vesicular protuberance of cell membrane. The componental and structural changes in the cell membrane of apoptotic cells may be recognized by adhesion molecules and phosphatidylserine receptors on the surface of phagocytes, thereby apoptosis cells are phagocytized and degraded. Thus apoptotic cells do not cause local inflammatory reaction and cause damages to neighbor tissues.

Apoptosis is an initiation and signal-dependent process, which can be induced by various factors, such as exposure to radiation, toxins, drugs, ischemia and hypoxia, viral infection, etc. It has been found from studies that most of these factors may trigger the apoptosis mechanism through activating the death receptors. Death receptors are cell surface receptors that transmit apoptosis signals initiated by specific ligands. They play an important role in apoptosis and can activate a caspase cascade within seconds of ligand binding. Induction of apoptosis via this mechanism is therefore very rapid. Death receptors belong to the tumor necrosis factor (TNF) gene superfamily and generally can have several functions other than initiating apoptosis. They belong to the superfamily of tumor necrosis factor receptors (TNFR) and, when coupling with corresponding ligands, can transmit the apoptotic signal into cells through a series of signal transduction processes. This procedure involves the proteins of multiple families, including TNF/TNFR superfamily, TNFR-associated factor (TRAF) superfamily, death structure domain proteins, etc., and finally causes the activation of the caspase protease family, the executor of apoptosis, which in turn shear the corresponding substrates to drive cells into apoptosis. The caspase protease family has been shown to be a kind of biomacromolecules, which plays a main role in the process of apoptosis. (*Apoptosis: Pharmacological Implications and Therapeutic Opportunities;* Kaufmann, S. H., Ed.; Academic Press: San Diego, 1997; *When Cells Die;* Lockshin, R. A., Zakeri, Z., Tilly, J. L., Eds.; Wiley-Liss: New York, 1998.)

Caspase proteases produce very important effects on the pathogenic course of neurodegenerative diseases [*Cell,* 75: 641-652 (1993); Science 263: 826-828, (1994)], which is one of the reasons they have been so thoroughly studied in recent years. Caspase-3 genes cause apoptosis of transfected Sf9 cells of an insect, and this process may be blocked by BCL-2. After removing caspase-3 from the extracting solution of apoptotic cells, the extract will lose the ability of inducing apoptosis, and when adding purified caspase-3, it will regain the ability. Knocking out the caspase-3(CPP32) gene can block the death of neuron in the process of cerebral development. Activated caspase-3 acts on many substrates, including the cytoskeleton, and causes apoptosis. Potentiation of caspase-3 activity has been proved in various diseases of the nervous system, such as experimental cerebral ischemia and hypoxia [Chen J, Nagayama T, Jin K, et al. *J Neurosci,* 18(13): 4914-4928 (1998); Namura S, Zhu J, Fink K, et al. *J Neurosci,* 18(10): 3659-3668( 1998)], cerebral trauma [Beer R, Franz G. Srinivasan A, et al. *J Neurochem,* 75(3): 1264-1273 (2000)]. Infarct volume may be reduced and therapeutic time window may be prolonged when treating with caspase-3 inhibitor in animal model of cerebral ischemia [Ma J, Endres M, Moskowitz M A., *Br J Pharmacol,* 124(4): 756-762 (1998)], which further supports the theory of caspase-3 playing an important role in apoptosis.

Further studies on the action of different caspases in the apoptosis process are limited by lack of small molecule inhibitors having a high selectivity to the different caspases [Garcia-Calvo, M.; Peterson, E. P.; Leiting, B.; Ruel, R.; Nicholson, D. W.; Thornberry, N. A. *J. Biol. Chem.* 273: 32608-32613 (1998); Schotte, P.; Declercq, W.; Van Huffel, S.; Vandenabeele, P.Beyaert, R. N., *FEBR Lett.* 442, 117-121. (1999)]. Although various peptide inhibitors with high activity have been reported, their use is greatly limited due to their moderate selectivity at most and poor cell permeability. Therefore, finding the novel small molecule non-peptide caspase inhibitors, especially with good selectivity, not only is important for the study of the mechanism of each type of caspase in the apoptosis process, but also is hopeful to develop some new drugs for treating neurodegenerative diseases, especially Alzheimer's disease, apoplexy and brain ischemic injuries.

SUMMARY OF THE INVENTION

An object of the present invention is to provide isoquinoline-1,3,4-trione compounds with new structure, which can be used as caspase inhibitors and nerve protectors.

Another object of the present invention is to provide a method for preparing the compounds.

Still another object of the present invention is to find the use of said compounds in preparation of medicine for treating neurodegenerative diseases, especially Alzheimer's disease, epilepsy and brain ischemic injuries etc.

The present invention employs a key reaction of oxidative deacylation to synthesize the isoquinoline-1,3,4-trione com-
} pounds, and enhances their enzyme inhibition activity and nerve protection effect by changing substitution of different functional groups.

BRIEF DESCRIPTION OF THE DRAWINGS

FIG. 1 shows the morphology of PC12 cells in 1% dimethyl sulfoxide.

FIG. 2 shows the morphology of PC12 cells in a mixture of 1% dimethyl sulfoxide and 20 μM Aβ.

FIG. 3 shows the morphology of PC12 cells in 200 nM Ac-DEVD-CHO.

FIG. shows the morphology of PC12 cells in a mixture of 200 nM Ac-DEVD-CHO and 20 μM Aβ.

FIG. 5 shows the morphology of PC12 cells in 28 μM chen-1.

FIG. 6 shows the morphology of PC12 cells in a mixture of 28 μM chen-1 and 20 μM Aβ.

FIG. 7 shows the effect of different Caspase-3 inhibitors on viability of apoptosis of PC12 induced by Aβ.

FIG. 8 shows the effect of Caspase-3 inhibitors with different concentration on viability of apoptosis of PC12 induced by Aβ.

FIG. 9 shows the results of flow cytometry of the effect on PC12 cells of Caspase-3 inhibitors and 20 μM Aβ.

FIG. 10 shows the effect of 20 μM Aβ and Caspase-3 inhibitors on the percentage of apoptosis of PC12.

FIG. 11 shows activity of PC12 cells treated with 20 μM Aβ and caspase-3 inhibitors for 10 hours, in which—☐—represents 1% dimethyl sulfoxide;—■—represents Aβ+ dimethyl sulfoxide;—▲—represents Aβ+2 μM Ac-DEVD-CHO;—x—represents Aβ+28 μM chen-1;—*—represents 2 μM Ac-DEVD-CHO,—●—represents 28 μM chen-1.

DETAILED DESCRIPTION OF THE INVENTION

In the present invention, a precursor compound, 3-acetyl-4-hydroxyl-isoquinoline-1-one, shown as structural principle

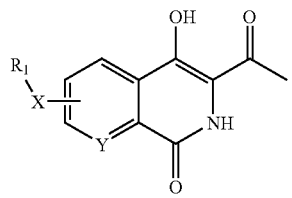

3-acetyl-4-hydroxyl-dihydroisoquinoline-1-ketone is used to synthesize isoquinoline-1,3,4-trione shown as structural formula I

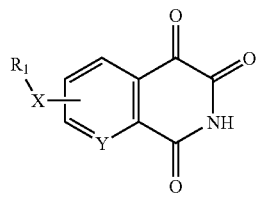

Dihydroisoquinoline-1,3,4-trione, and the amino group of the above compound is substituted by different functional group to further synthesize the isoquinoline-1,3,4-trione shown as structural formula II

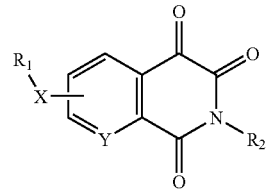

Dihydroisoquinoline-1,3,4-trione wherein, the substituent $R_1$ may be one, two or three groups optionally selected from the group consisting of H; alkyl; hydroxyl; alkyl substituted by the groups including halogen, alkoxyl or hydroxyl; alkoxyl or alkylamino substituted by the groups including halogen, alkoxyl or hydroxyl; $C_2$-$C_6$ alkenyl substituted by oxygen or amine; $C_3$-$C_6$ cycloalkyl; substituted aryl; benzyl; alkanoyl; alkanoyl substituted by the groups including halogen, alkoxyl or hydroxyl; $C_2$-$C_6$ enoyl; $C_3$-$C_6$ cycloalkanoyl; tert-butoxycarbonyl; benzoyl; benzoyl substituted by one, two or three groups including alkylamino; benzylacyl; benzylacyl substituted by one, two or three groups including alkylamino; thienoyl; adamantylcarbonyl; mandeloyl; alkoxyl; alkylamino; cycloalkoxyl; cycloalkylamino; amino; acylamino; alkyloxycarbonyl; cycloalkoxycarbonyl; alkanoylxy; alkanoylamino; cycloalkyanoylxy; cycloalkanoylamino; ureido; urenylene; alkanoyl; nitro; carboxyl;

$R_2$ is H; alkyl; alkyl or $C_3$-$C_6$ cycloalkyl, which are substituted by the groups including halogen, alkoxyl or hydroxyl; $C_2$-$C_6$ alkenyl; aryl; substituted aryl;

X is $CH_2$, NH, or O; Y is CH, or N.

A preferable compound of the present invention is isoquinoline-1,3,4-trione compounds with structure formula I wherein $R_1$ is

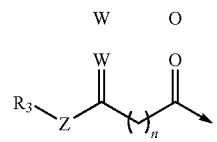

substituent $R_3$ may be one, two or three groups optionally selected from the group consisting of H; alkyl; hydroxyl; alkyl substituted by the groups including halogen, alkoxyl or hydroxyl; alkoxyl or alkylamino substituted by the groups including halogen, alkoxyl or hydroxyl; $C_2$-$C_6$ alkenyl substituted by oxygen or amine; $C_3$-$C_6$ cycloalkyl; substituted aryl; benzyl; alkanoyl; alkanoyl substituted by the groups including halogen, alkoxyl or hydroxyl; $C_2$-$C_6$ enoyl; $C_3$-$C_6$ cycloalkanoyl; tert-butoxycarbonyl; benzoyl; benzoyl substituted by one, two or three groups including alkylamino; benzylacryl; benzylacrylcarbonyl substituted by one, two or three groups including alkylamino; thienoyl; adamantylcarbonyl; mandeloyl; alkoxyl; alkylamino; cycloalkoxyl; cycloalkylamino; amino; acylamino; alkyloxycarbonyl; cycloalkoxycarbonyl; alkanoylxy; alkanoylamino; cycloalkyanoylxy; cycloalkanoylamino; ureido; urenylene; alkanoyl; nitro; carboxyl;

Z is $CH_2$, O or NH; W is O or $H_2$;

n=1, 2, 3, 4, or 5;

The method of the present invention is carried out by the following steps: According to the chemical reaction formula,

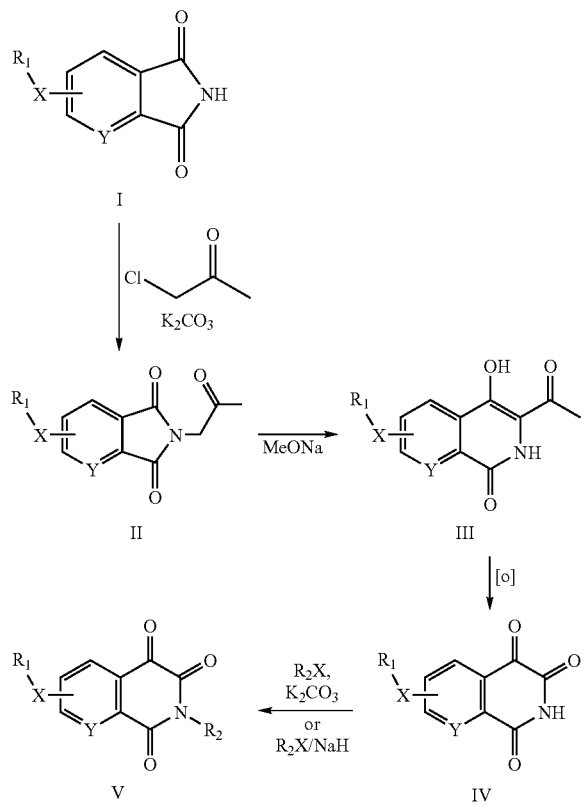

Compound II is synthesized from compound I according to the method of (Manske, R. H. F. Benzyl Phthalimide Organic Synthesis Coll. Vol. 2, 83-84). And compound II in a solvent such as methanol, ethanol, dimethylformamide, benzene, toluene etc is subjected to a further reaction in the presence of excess sodium ethoxide to obtain compound III. Then the parent compound IV is obtained from compound III in a suitable solvent such as dimethyl sulfoxide, dimethylformamide, toluene etc with air inputted into through the key reaction of oxidative deacylation at a temperature of 80° C. to 120° C. The reaction time depends on the characters of the reactant's activating group (or compound IV is obtained under other oxidation condition, such as mixed acid condition). Then compound IV reacts with potassium carbonate (or sodium hydride) and halogenated hydrocarbon in an anhydrous solvent such as dimethyl sulfoxide, dimethylformamide, dichloromethane, benzene, tetrahydrofuran, acetone etc to obtain compound V. After the reaction is completed, the reaction is typically quenched with ice water, and the resultant mixture is extracted with ether, acetic ether, dichloromethane, chloroform etc, and then washed with 5% hydrochloric acid, water, saturated salt solution in turn, dried, removed the solvent under reduced pressure at low temperature. The final products are obtained through column chromatography. The yield ranges from 30% to 50% depending on the characters of reactant IV and halogenated hydrocarbon. The resultant product is identified by the methods of NMR or mass spectrum.

Hereinafter, the enzyme inhibition activity and the protection effect on apoptotic cells of the compounds according to the present invention are illustrated by the pharmacological tests (The tests are described in detail, including reagents, apparatus, detailed steps, etc, and the full name is used instead of abbreviated notation)

EXAMPLE 1

Inhibition of the Compounds in the Present Invention to Activity of Caspase-3

1. Preparation of Active Caspase-3 Recombination Protein

In a expression system of *Escherichia coli,* large and small subunits (P17 and P12) of caspase-3 were expressed respectively in vitro with pGEMEX-I vector, BL21(DE$_3$)/pLysS strain (Promega, Madison, Wis., U.S.A.). 1 liter of expression bacteria were washed three times with 100 ml of celiclastic solution (pH7.5, containing 50 mM Tris.Cl, 100 Mm NaCl, 2mM edetic acid), and the bacteria were resuspended in cellclastic solution and 1% Trion-100. Then the bacteria were broken using ultrasonic wave in an ice bath, and centrifuged at 12000 g lower than 4° C. for 15 minutes, the supernatant was discarded. Both the two fragments, P17 and P12, existed in precipitation in the form of inclusion bodies. The precipitation was washed with urea of 1M, 2M, 3M in turn to remove most of heteroprotein, and finally dissolved in 6M of urea, 2 mM of dithiothreitol respectively. The purification was performed using HiPrep 16/10 QXL anion exchange column and FPLC system. When purifying P17 subunits, the solutions running through Q column were Buffer A (50 mM Tris.Cl pH7.2, 6M urea, 1 mM DTT) and Buffer B (Buffer A+1M NaCl). The sample to be purified was injected into the HiPrep 16/10 QXL column equilibrated with Buffer A, and eluted with Buffer A firstly, then eluted with linear NaCl gradient elution composed of Buffer A and 100% Buffer B. Next protein peak was eluted when electric conductance reached 20 mS/min. When purifying P12 subunits, the solutions running through Q column were Buffer A (50 mM Tris.Cl pH7.8, 6M urea, 2 mM DTT) and Buffer B (Buffer A+1M NaCl) respectively. The sample to be purified was injected into the Q column equilibrated with Buffer A, and eluted with Buffer A, then eluted with linear NaCl gradient elution composed of Buffer A and 100% Buffer B. Each one-protein peak was eluted when the electric conductance was 0 mS/min and 20 mS/min. The flow rate of elution was 2 ml/min, one tube of eluant was collected every two minutes. The composition and purity of protein in the collected fractions were checked using SDS-PAGE, and the fractions with higher purity were combined according to the testing result and the concentration curve of protein and stored at a temperature of 4° C. When pH value of the solution is higher than 4.9, the P17 subunits carry negative charges and can bind to Q-Sepharose by electrostatic interaction. As the increase of the concentration of salt ion in the eluant, each protein component binding on Q-Sepharose were eluted in turn according to the strength of electrostatic force, thereby obtaining single band of P17 subunits through separation and purifying. When pH value of the solution equal to 7.8, the P12 subunits substantially don't carry any electric charges, while most of other heteroproteins carry negative charges and can bind to Q-Sepharose by electrostatic interaction. P12 subunits contained in the sample to be purified were injected into Q-Sepharose and flow out without binding with chromatographic column, and the heteroproteins carrying negative charges bound to the chromatographic column and separated from P12 subunits, thereby obtaining single band of P12 subunits. After purified P17 subunits were mixed with purified P12 subunits in a ratio of 1:1 at the temperature of 4° C., the sample was added drop wise into a renaturation buffer in a ratio of 1:15, stirring overnight. The renaturation buffer (pH7.5) contained 50 mM Tris.Cl, 100 mM NaCl, 2 mM dithiothreitol, 10% sucrose, 5 mM edetic acid. Active recombinant caspase-3 was obtained after renaturation. The P17 and P12 subunits not forming active caspase-3 can be removed with a hydrophobic column.

EXAMPLE 2

Activity Inhibition Reaction of Caspase-3 [Gurtu V. et al, *Analyt. Biochm.*, 251. 98-102(1997)]

The activity of caspase-3 was detected in 50 mM Tris.Cl, pH7.5, 100 mM NaCl, 100 mM dithiothreitol, 100 µM Ac-Asp-Glu-Val-Asp-p-nitroaniline (Bachem Bioscience, Pa., U.S.A.) at 35° C. After the specific substrates, Ac-Asp-Glu-Val-Asp-p-nitroaniline, were cleaved by caspase-3, the released p-nitroaniline had a characteristic light absorption at OD405 nm. Thus the activity of caspase-3 may be detected dynamically using SpectraMAX340 according to the change of the light absorption value. Activity inhibition reaction of caspase-3 was performed on a 96-well plate with 100 µl of total reaction volume, which contained 2 µl of test compound dissolved in dimethyl sulfoxide, and in 100 nM caspase-3 enzyme solution.

2. Detection of Inhibition Activity of Compounds

A compound of different concentration of mother solution was dissolved in dimethyl sulfoxide. 2 µl of the solutions were added to a reaction system of caspase-3 when conducting reaction. The compound with different concentration had different inhibition effect on the activity of caspase-3, which corresponded to different activity value respectively. Dimethyl sulfoxide free of the compounds was used as a negative control, and the inhibitor Ac-Asp-Glu-Val-Asp-aldehyde (IC50=34 nM) (Bachem Bioscience, Pa., U.S.A.) was used as a positive standard control. $IC_{50}$ for caspase-3 of these compounds could be obtained based on the experimental data. The $IC_{50}$ values reflect the inhibition effect of the compounds on caspase-3 directly. The results are as shown in table 1.

TABLE 1

Inhibition effect of part of the compounds in the present invention on the activity of caspase-3

| Compound | Structure | Caspase Inhibition ($IC_{50}$, M) |
|---|---|---|
| Chen-1 | 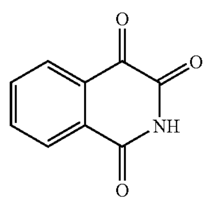 | 0.588 |
| Chen-2 | 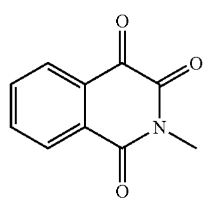 | 0.896 |
| Chen-3 | 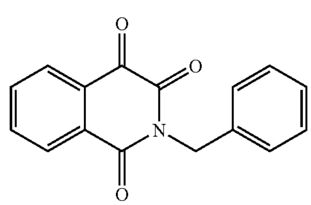 | 1.663 |
| Chen-4 | 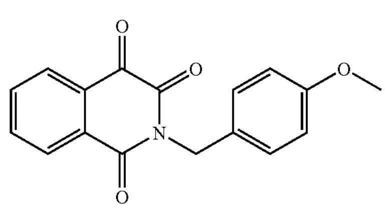 | 1.634 |
| Chen-5 | 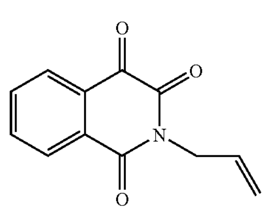 | 1.517 |

TABLE 1-continued
Inhibition effect of part of the compounds in the present invention on the activity of caspase-3
| Compound | Structure | Caspase Inhibition (IC$_{50}$, M) |
|---|---|---|
| Chen-6 | 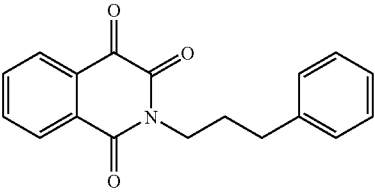 | 1.168 |
| Chen-7 | 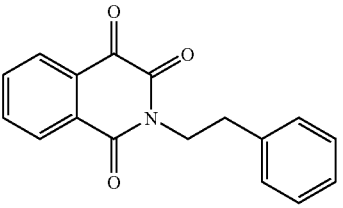 | 3.321 |
| Chen-8 | 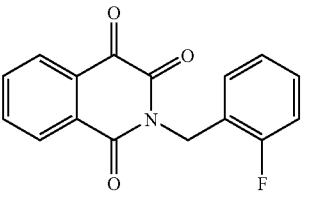 | 0.803 |
| Chen-9 | 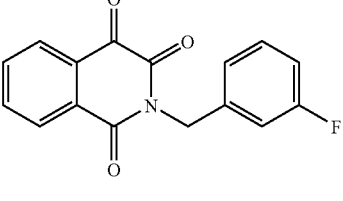 | 1.390 |
| Chen-10 | 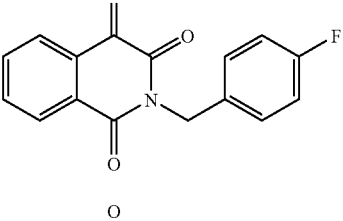 | 0.522 |
| Chen-11 | 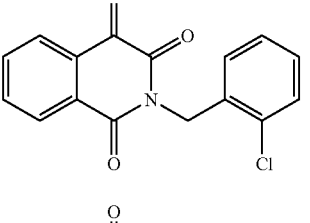 | 0.563 |
| Chen-12 | 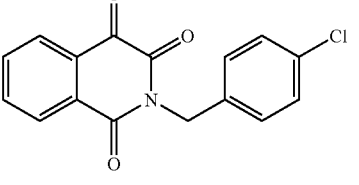 | 0.685 |

TABLE 1-continued

Inhibition effect of part of the compounds in the present invention on the activity of caspase-3

| Compound | Structure | Caspase Inhibition (IC$_{50}$, M) |
| --- | --- | --- |
| Chen-13 | $R_1$ = NO$_2$, $R_2$ = H<br>$R_1$ = H, $R_2$ = NO$_2$ | 0.588 |
| Chen-14 | 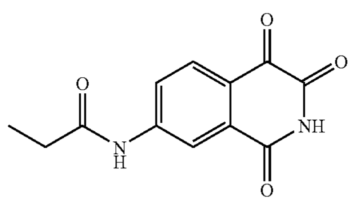 | 1.421 |
| Chen-15 | 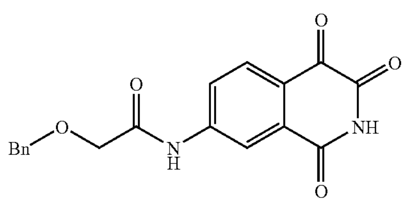 | 1.301 |
| Chen-16 | 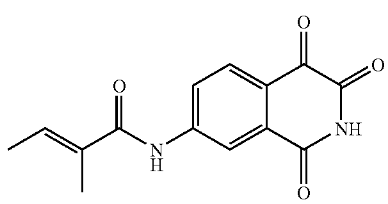 | 9.115 |
| Chen-17 | 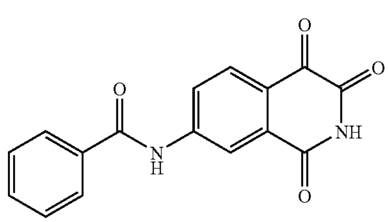 | 2.120 |
| Chen-18 | 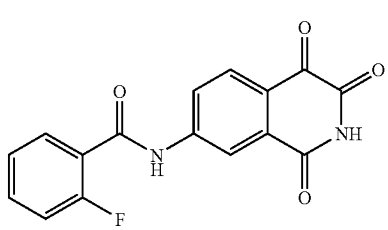 | 0.813 |

TABLE 1-continued

Inhibition effect of part of the compounds in the present invention on the activity of caspase-3

| Compound | Structure | Caspase Inhibition (IC$_{50}$, M) |
| --- | --- | --- |
| Chen-19 | 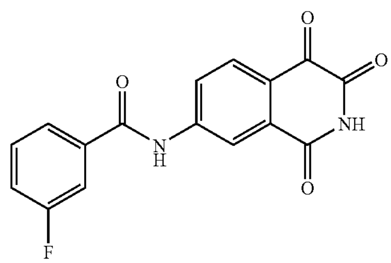 | 0.617 |
| Chen-20 | 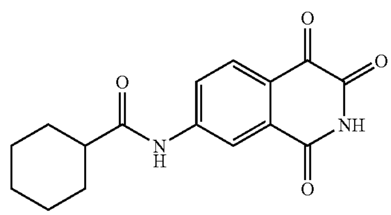 | 0.797 |
| Chen-21 | 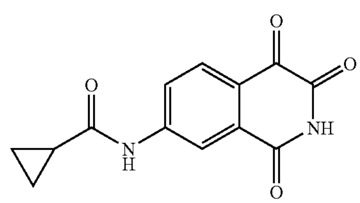 | 0.577 |
| Chen-22 | 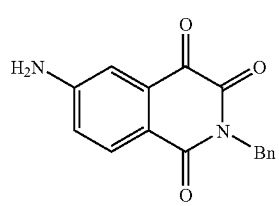 | 3.514 |
| Chen-23 | 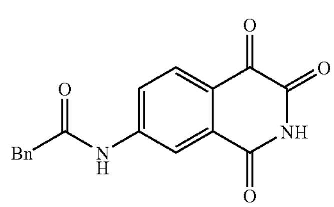 | 0.397 |
| Chen-24 | 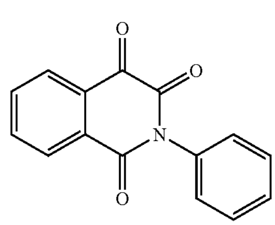 | 5.038 |

TABLE 1-continued

Inhibition effect of part of the compounds in the present invention on the activity of caspase-3

| Compound | Structure | Caspase Inhibition (IC$_{50}$, M) |
|---|---|---|
| Chen-25 | 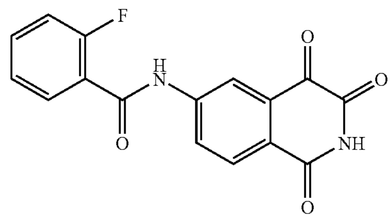 | 1.324 |
| Chen-26 | 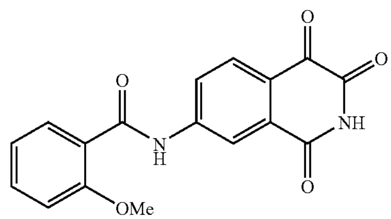 | 0.317 |
| Chen-27 | 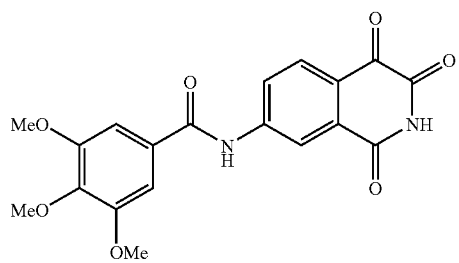 | 0.897 |
| Chen-28 | 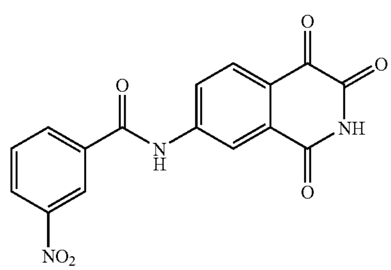 | 2.080 |
| Chen-29 | 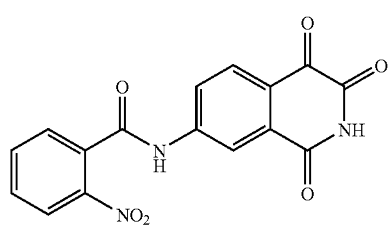 | 0.435 |
| Chen-30 | 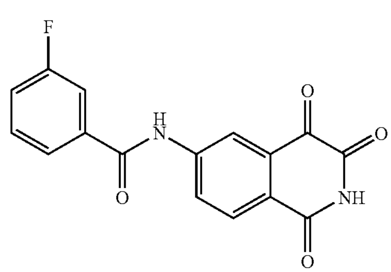 | 0.742 |

TABLE 1-continued

Inhibition effect of part of the compounds in the present invention on the activity of caspase-3

| Compound | Structure | Caspase Inhibition (IC$_{50}$, M) |
| --- | --- | --- |
| Chen-31 | 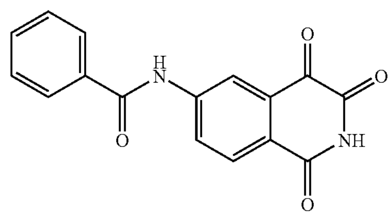 | 0.438 |
| Chen-32 | 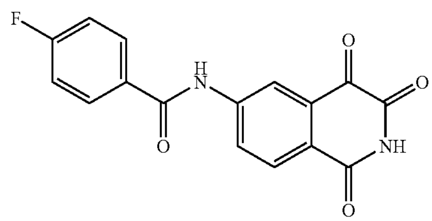 | 0.768 |
| Chen-33 | 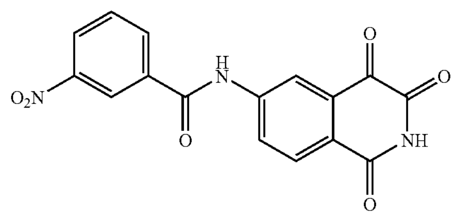 | 4.720 |
| Chen-34 | 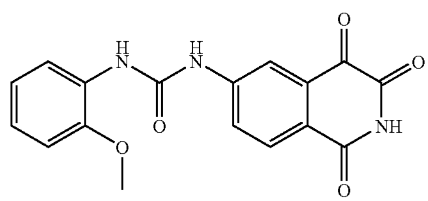 | 0.351 |
| Chen-35 | 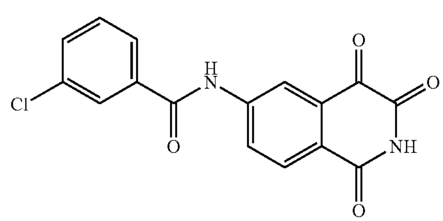 | 0.492 |
| Chen-36 | 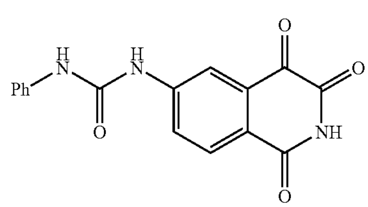 | 0.329 |
| Chen-37 | 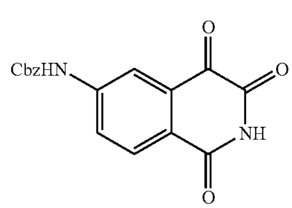 | 1.009 |

TABLE 1-continued

Inhibition effect of part of the compounds in the present invention on the activity of caspase-3

| Compound | Structure | Caspase Inhibition (IC$_{50}$, M) |
| --- | --- | --- |
| Chen-38 | 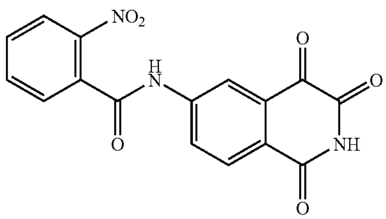 | 0.281 |
| Chen-40 | 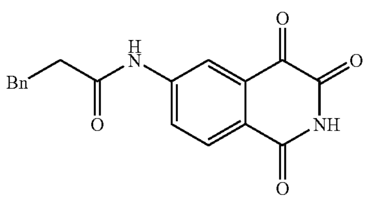 | 0.535 |
| Chen-41 | 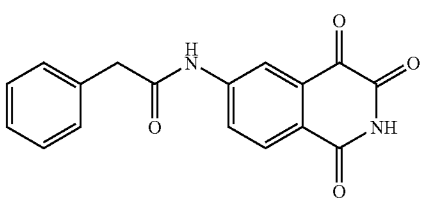 | 0.304 |
| Chen-42 | 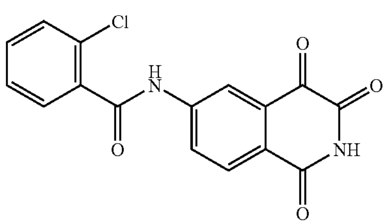 | 0.252 |
| Chen-43 | 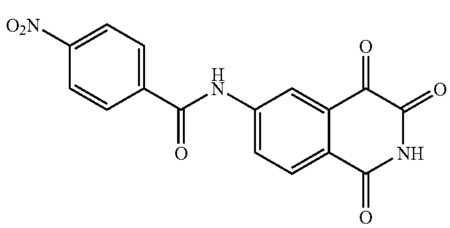 | 0.246 |
| Chen-44 | 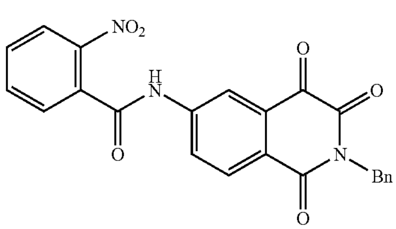 | 0.581 |

TABLE 1-continued

Inhibition effect of part of the compounds in the present invention on the activity of caspase-3

| Compound | Structure | Caspase Inhibition (IC$_{50}$, M) |
|---|---|---|
| Chen-45 | 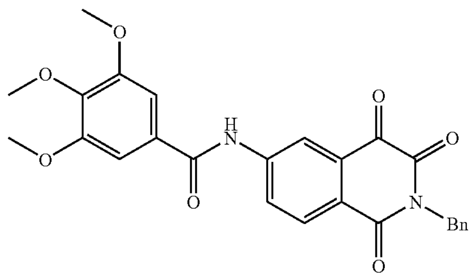 | 1.094 |
| Chen-46 | 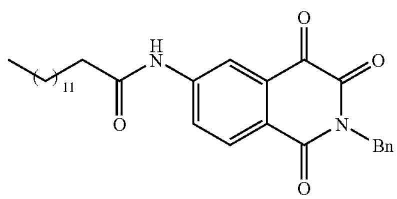 | 11.71 |
| Chen-47 | 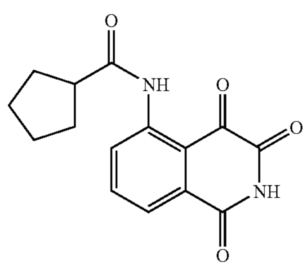 | 0.329 |
| Chen-54 | 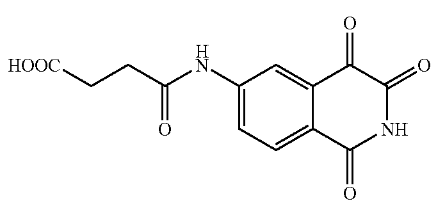 | 0.095 |
| Chen-55 | 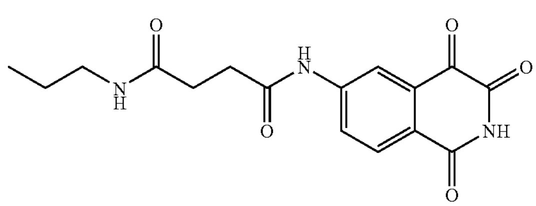 | 0.143 |
| Chen-56 | 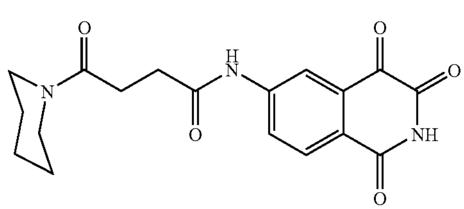 | 0.136 |

TABLE 1-continued

Inhibition effect of part of the compounds in the present invention on the activity of caspase-3

| Compound | Structure | Caspase Inhibition (IC$_{50}$, M) |
| --- | --- | --- |
| Chen-57 | 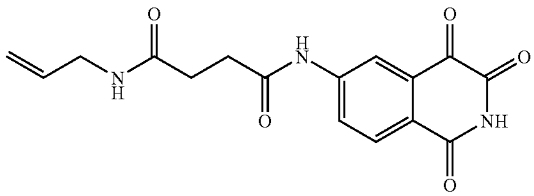 | 0.115 |
| Chen-58 | 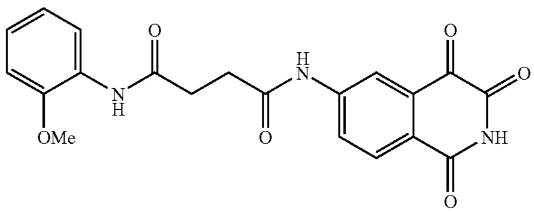 | 0.080 |
| Zhang-3 | 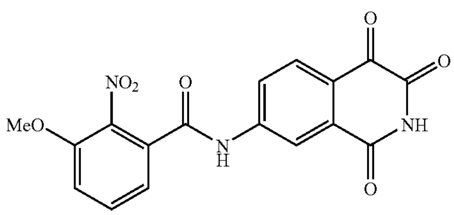 | 6.259 |
| Zhang-4 | 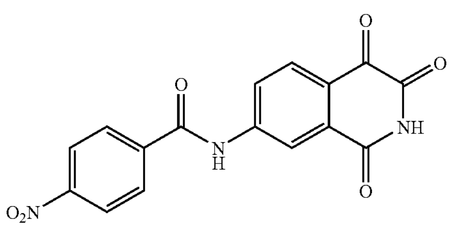 | 1.152 |
| Zhang-6 | 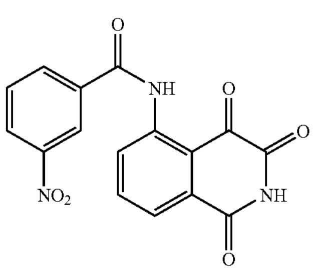 | 0.111 |
| Zhang-7 | 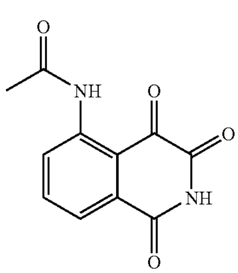 | 0.536 |

TABLE 1-continued

Inhibition effect of part of the compounds in the present invention on the activity of caspase-3

| Compound | Structure | Caspase Inhibition (IC$_{50}$, M) |
|---|---|---|
| Zhang-8 | 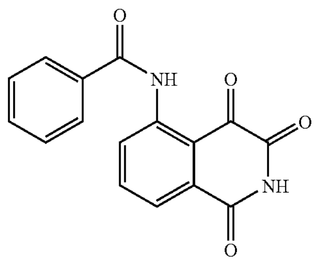 | 0.361 |
| Zhang-9 | 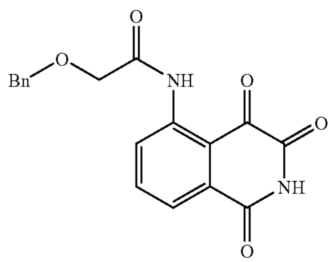 | 0.440 |

EXAMPLE 3

Protection Effect of the Compounds in the Present Invention for Apoptosis Cells (PC12)

Materials: Inhibitors of caspase-3 were dissolved in dimethyl sulfoxide in different concentration of mother solution, and the final concentration in use was determined according to requirement, wherein the concentration of dimethyl sulfoxide was between 0.5% and 1%; the concentration of positive inhibitor, Ac-Asp-Glu-Val-Asp-aldehyde, in mother solution was 20 μM-2 mM; apoptosis inducer, β-amyloid (AP25-35) (purchased from Sigma), was prepared to mother solution of 1 mM with distilled water, and the final concentration in use was 20 μM.

Culture of cells: PC 12 cells were obtained from XiCan Tang of Institute of Material Medica, CAS. Media were DMEM(HG) containing 10% calf serum. PC12 were incubated in an incubator with constant temperature with 5% carbon dioxide at 37° C. The cells were inoculated in Petri dishes and 96-well plates in the amount of $3 \times 10^4/cm^3$, the compounds of the present invention were added into after 12 hours, and 20CM of apoptosis inducer, Aβ$_{25-35}$, was added after 24 hours. The cells were collected at different time and used to detect the protection effect of the compounds of the present invention on apoptotic cells using various detection method of apoptosis.

Results of Apoptosis Tests:

1. Morphological Comparison

Two inhibitors, 200 nM of Ac-Asp-Glu-Val-Asp-aldehyde and 28 μM of chen-1, were respectively added into PC12 culture, and 20 μM of Aβ was added after 12 hours. After 72 hours, it can be observed obviously under phase contrast microscope that PC12 under different treatment have significant difference morphologically (see FIGS. 1-6). As shown, 20 μM of Aβ exhibit remarkable toxicity for PC12, appearing as typical characteristics of apoptosis: cell aggregation, nucleus contraction, losing cellar morphological features, and apoptotic bodies. However, caspase-3 inhibitors have distinct resistant effect on apoptosis of PC12 mediated by neurotoxicity of Aβ. Moreover, 1% dimethyl sulfoxide, high concentration of chen-1 and low concentration of Ac-Asp-Glu-Val-Asp-aldehyde exhibit no toxic effect on PC12 cells.

2. Detection of Cell Viability Using Microculture Tetrozolium (MTT)

After PC 12 cells have been cultured for 24 hours, caspase-3 inhibitors were added into, and Aβ$_{25-35}$ (20 μM) was added to induce apoptosis after another 8 hours. Wherein Ac-DEVD-CHO was 2 μM; chen-1, chen-2 and chen-3 was 5 μg/mL. Cell viability was detected by MTT method after culturing the cells for 48 hours at 37° C.

PC12 cells were inoculated in different 96-well culture plates in an amount of $3 \times 10^4/cm^3$, then were incubated in $CO_2$ incubator (5% $CO_2$, 95% air) at 37° C. Caspase-3 inhibitors of different concentrations were added after 24 hours, and 20 μM of Aβ$_{25-35}$ was added to induce apoptosis after another 8 hours. Each had three repeated wells. Wherein the concentration of Ac-DEVD-CHO was 20 μM, 10 μM, 5 μM, 1 μM, 0.5 μM, and 0.1 μM respectively; the concentration of chen-1 was 60 μM, 30 μM, 20 μM, 10 μM, 5 μM, and 1 μM respectively. The cell viability was detected by MTT method after culturing the cells for 48 hours at 37° C.

The test results are shown in FIG. 7 and FIG. 8. 3. Flow Cytometry Detection $2 \times 10^6$ cells were collected at different time respectively after PC12 were treated in the same method. Cell precipitation was washed twice with PBR, followed by adding ice ethanol, and the resulting solution was blown to disperse the cells into single, fixed for 2 hours at 4° C. Before staining, the solution was centrifuged at 300 rpm for 10 minutes, and the supernatant was discarded, then the precipitation was washed twice with PBR to remove ethanol substantially. Into the cell precipitation was added a staining solution (containing 0.1% TritonX-100, 0.1 mM EDTApH7.4, 0.01 mg/ml RNase A, 50

μg/ml propidium iodide). Cell fluorescence was detected with flow cytometry after the cells in staining solution for 30 minutes at 4° C. away from light, and percentage and cycle of apoptotic cells were calculated by analyzing DNA content. The results were obtained by flow cytometry laboratory of Institute of Biochemistry and Cell Biology, CAS. The results of flow cytometry are shown in FIGS. 9 and 10.

$A\beta_{25\text{-}35}$ acted on PC12 cells for 24, 48, 72 hours respectively, a typical "sub-$G_1$ peak" could be seen in DNA content-frequency histogram, which increased as extension of action time of $A\beta_{25\text{-}35}$, and the percentage of apoptotic cells was 4.73%, 19.91%, 31.71% respectively. After 72 hours, the percentage of apoptotic cells of the negative control without adding $A\beta_{25\text{-}35}$ and the sample only with caspase-3 inhibitor added was 1.89%, 2.27%, 2.15% respectively, all belonging to normal range. While when $A\beta_{25\text{-}35}$ and caspase-3 inhibitors, i.e. 2 μM Ac-DEVD-CHO, 28 μM Chen-1, existed in the medium at the same time, the percentage of apoptotic cells was 4.01%, 4.09% respectively, which were obviously much smaller than that only with $A\beta_{25\text{-}35}$ added. As illustrated from the above results, it may be seen that caspase-3 inhibitors could protect PC12 markedly and resist apoptosis of PC12 mediated by neurotoxicity of $A\beta$ of $A\beta_{25\text{-}35}$, and they have no toxicity in low concentration themselves. It was found that both $A\beta_{25\text{-}35}$ and caspase-3 inhibitors didn't influence cell cycle when analyzing the cycle of non-apoptotic cells.

4. Detection of Caspase-3 Activity

After treating PC12 in the same method, 20 μM of $A\beta_{25\text{-}35}$ was added into, the cells were blown down and collected after 10 hours, and centrifuged at 200 rpm for 10 minutes. A cellclastic solution (50 mM Tris.HCl pH7.5, 5 mM $MgCl_2$, 2 mM DTT, 2 mM PMSF, 10 μg/ml Papstatin A, 10 μg/ml leupeptin) was added after cell precipitation was washed twice with PBR. The cell lysate was centrifuged at 12000 rpm, 4° C. for 15 minutes after subjected to four "freeze-thawing" cycles; the supernatant was taken for detection of enzyme and protein. The total volume of the reaction system was 100 μl, wherein containing 50 mM Tris.HCl pH7.5, 10 mM DTT, 0.1%CHAPS, 2 mM EDTA, 100 mM NaCl, 200 μM Ac-DEVD-pNA, into which protein samples with the same quality were added. The reaction was conducted at 37° C. for 4 hours, and light absorption values at wavelength of 405 nm were measured at each interval of 30 minutes in SpectraMAX340 apparatus. The results are shown in FIG. 11, indicating that the rate of hydrolyzing Ac-DEVD-pNA was different in each sample under the condition of identical protein quality 10 hours after adding 20 μM of $A\beta$. Caspase-3 activity in the samples only with $A\beta_{25\text{-}35}$ added were obviously higher than those in negative control without adding $A\beta_{25\text{-}35}$, in the samples only with caspase-3 added, and in the samples with $A\beta_{25\text{-}35}$ and inhibitor added simultaneously, indicating that activated caspase-3 and cells about to undergoing apoptosis contained in these samples were more than that contained in other samples. By detecting activity of caspase-3, the results indicated specifically that caspase-3 inhibitors resisted apoptosis of PC12 mediated by neurotoxicity of $A\beta$ of $A\beta_{25\text{-}35}$, thereby protecting cells from injury.

Advantageous Effects:

1. The present invention provides a kind of novel isoquinoline-1,3,4-trione compounds and the preparation method thereof.

2. The compounds of the present invention have remarkable inhibition to caspase, and have superior protection to apoptotic cells, thus can be used as caspase inhibitors and nerve protectors.

3. The present invention provides a route for developing the medicines for treating neurodegenerative diseases, especially Alzheimer's disease, apoplexy and brain ischemic injuries et al.

[1]HMR was measured with Varian MercuryAMX300 type apparatus; MS was measured with VG ZAB-HS or VG-7070 type apparatus, all were EI source (70 ev) except noted; all solvents were subjected to re-distillation before used, all anhydrous solvents used were obtained by drying process according to standard method; except explained specifically, all reactions were performed under protection of argon and tracked with TLC, when conducting after treatment all were subjected to washing procedure with saturated salt solution and drying procedure with anhydrous magnesium sulfate; except explained specifically, purification of products was conducted by using silica gel (200-300 mesh) column chromatography; the silica gel used, including 200-300 mesh and $GF_{254}$ were manufactured by Qingdao Haiyang Chemical Co. Ltd and Yantai Yuanbo Silica Gel Company.

EXAMPLE 4

Preparation of Compound Chen-3

-continued

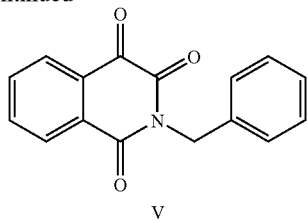

V 2.0 g of compound I was mixed with 3.76 g of potassium carbonate thoroughly, then the resulting mixture was poured into a 25 mL flask followed by the addition of 4.0 mL of chloroacetone. The resultant solution was then heated the to 90-110° C. (a reflux condensing tube was needed to be equipped on the flask, and the system was protected with argon) the solution was stirred, while maintaining the temperature at 90-110° C., and the reaction was conducted for 3-4 hours. After the reaction was completed, excess chloroacetone was removed under a reduced pressure, into the residue was added a great deal of water, then filtrated with Buchner's filter. The resultant solid was washed twice with 10 mL of 10% NaOH and 5-6 times with water respectively, dried under vacuum to obtain compound II.

After a reflux condensing tube and a dropping funnel were connected on a three-necked bottle, 100 mL of absolute methanol (or other anhydrous solvent) was added into the three-necked bottle, followed by slowly adding 0.23 g of metallic sodium (or directly adding 10 mmol of sodium methoxide). After the solid dissolved entirely, the solution was heated and refluxed, and then compound II was dissolved in absolute methanol (60 mL $CH_3OH$ and 1.0 g compound II) and added to the solution using a dropping funnel. After conducting the reflux for 2 hours the reaction was processed as follows: the system was cooled with ice water bath, and slowly neutralized with 1M hydrochloride, and stirred for 30 min in ice water bath after which a large amount of solid emerged, which was filtrated to obtain a solid. The resultant solid was then washed with small amount of water, and dried in vacuum, thereby obtaining compound III.

230 mg of compound III was placed in a 25 mL flask followed by the addition of 5 mL of the solvent listed in the above, air was continuously blown into the solution by a bubbler. The reaction was completed after 10 hours and processed as follows: the reaction solution was diluted with 30 mL of acetic ether, extracted with water, and the water phase was back-extracted back-extracting with 30 mL of acetic ether, the organic phases were washed with water and saturated salt solution respectively, the organic phases were washed and then dried and condensed. The residue was applied on silica gel column (petroleum ether: acetic ether=2:1) to obtain compound IV.

(Another Method for Preparing Compound IV):

3 mL of concentrated sulfuric acid were placed in a 10 mL beaker followed by the slow addition of 0.5 ml of fuming nitric acid. The system was cooled in an ice-water bath. 500 mg of compound III were added into the above solution when the temperature fell to less than 12° C., it could be seen at once that the color of the reaction solution changed into deep red, the temperature also rose to more than 50° C. instantly. The raw material was shown to have disappeared by TLC analysis after 5 minutes, and the reaction was processed as follows: 50 mL of acetic ether were added to dilute the reaction solution. The solution was extracted with water, and the resultant water phase was back-extracted with 30 mL of acetic ether. The organic phases were washed with water and saturated salt solution respectively. The organic phases were then combined, dried and condensed, thereby obtaining product IV.

40 mg of compound IV were dissolved in 1.5 mL of anhydrous solvent (listed above); the system was cooled in ice salt bath. The reaction was then commenced upon the addition of 14 mg of sodium hydride and allowed to proceed for 30 min after which 0.20 mL of benzyl chlorine were slowly dropped into the solution. The reaction was progressed for 3 hours: after which it was quickly extracted dichloromethane, dried, condensed, and the resultant residue was applied on silica gel column (petroleum ether: acetic ether=8:1) to obtain compound V.

EXAMPLE 5

Preparation of Compound Chen-13

After 4.0 g of 5-nitro-phthalimide were mixed with 5.74 g of potassium carbonate thoroughly, the resulting mixture was poured into a 25 mL flask followed by adding 6.6 mL of chloroacetone, and heated to 90-110° C. (a reflux condensing tube was needed to be equipped on the flask, the system was protected with argon). After the reaction was conducted for 3-4 hr, excess of chloroacetone was removed under a reduced pressure, into the residue was added a great deal of water, then filtrated with Buchner's filter. The resulting solid was washed twice with 10 ml of 10% NaOH, and 5-6 times with water respectively, dried in vacuum to obtain 5-nitro-N-(2-carbonyl-propyl)-phthalimide;

After a reflux, a condensing tube and a dropping funnel were connected on a three-necked bottle, 240 mL of absolute methanol was added into the three-necked bottle, followed by slowly adding 0.24 g of metallic sodium. After sodium was entirely dissolved, the solution was heated and refluxed, and then 5-nitro-N-(2-carbonyl-propyl)-phthalimide dissolved in absolute methanol (60 mL $CH_3OH$ and 1.0 g compound) was dropped into the solution by dropping funnel. After conducting the reflux for 2 hours the reaction was processed as follows: the system was cooled in ice water bath, slowly neutralizing the reaction was slowly neutralized with 1M hydrochloride, and to stirred for 30 min in ice water bath after which a large amount of solid emerged. The solution was centrifuged to obtain solid, the solid was dried under vacuum after washing with water, thereby obtaining 0.86 g of a mixture of 3-acetyl-4-hydroxyl-6-nitro-3,4-dihydro-isoquinolin-1-one and 3-acetyl-4-hydroxyl-7-nitro-3,4-dihydro-isoquinolin-1-one;

3 mL of concentrated sulfuric acid was placed in a 10 mL beaker followed by the addition of 0.5 mL of fuming nitric acid slowly; the system was cooled in ice water bath. 600 mg of the mixture manufactured in the above was added into the above solution when the temperature fell to less than 12° C., it could be seen at once that the color of the reaction solution changed into deep red, the temperature also rose to more than 50° C. The raw material disappeared by TLC analysis after 30 minutes, and the reaction was processed as follows: 50 mL of acetic ether were added to dilute the reaction solution, it was extracted with water, the water phase was back-extracted with 50 mL of acetic ether, the organic phases were washed with water and saturated salt solution respectively, the organic phases were combined, then dried and condensed, thereby obtaining Chen-13.

EXAMPLE 6

Preparation of Compound Chen-17

3.0 g of 2-carboxymethyl-benzoic acid were dissolved in 16 ml of fuming nitric acid. 16 ml of ice water was added into the resulting solution after stirred at room temperature for 2 hr, then filtrated to obtain a precipitation, dried in vacuum to obtain 1.99 g of 5-nitro-2-carboxymethyl-benzoic acid.

230 mg of 5-nitro-2-carboxymethyl-benzoic acid was placed in a 10 ml flask followed by adding 1 mL of ammonia water. The resulting mixture was heated and fluxed for 30 min to evaporate the solvent. Then the system was heated to 150° C. under reduced pressure by oil pump, after progressed for 20 min the reaction was processed as follows: the solid is dissolved with acetone and applied on silica gel column (petroleum ether: acetic ether=1:1) to obtain 7-nitro-4H-isoquinoline-1,3-dione.

35 mg of 7-nitro-4H-isoquinoline-1,3-dione were dissolved in 3 mL of acetic ether. After reduced with Pd/C the resulting mixture was filtrated to remove solid. Into the system is added 40 μL of pyridine and 50 μL of benzoyl chloride, and the reaction was processed after 3 hr: 20 mL of acetic ether were added to dilute the reaction solution, which was extracted with water, and the water phase was back-extracted with 20 mL of acetic ether, the organic phases were washed with water and saturated salt solution respectively, the organic phases, were combined then dryed and condensed. The resultant residue was transferred to a 10 mL flask followed by the addition of 2 mL of dry toluene (or dioxane) and 25 mg of selenium dioxide. After conducting heating and reflux for 12 hr the reaction was processed as follows: 20 mL of acetic acid were added to dilute the reaction solution, it was extracted with water, and the water phase was back-extracted with 20 ml of acetic ether, the organic phases were with water and saturated salt solution respectively, the organic phases were combined and then dried and condensed. The residue was applied on silica gel column (petroleum ether: acetic ether=1:1) to obtain chen-17.

The compounds listed in the following table were prepared in a method similar to that in the above:

| Compound number | Chemical structure | $^1$H-NMR |
|---|---|---|
| Chen-1 | 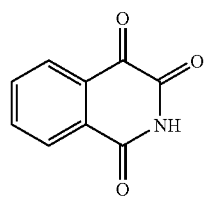 | δ(DMSO 300MHz) 11.97 (br, 1H), 8.13 (d, J=7.2 Hz, 1H), 8.05 (d, J=7.5 Hz, 1H), 7.95-7.88 (m, 2H) |
| Chen-2 | 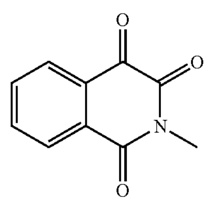 | δ(CDCl$_3$ 300MHz) 8.36 (dd, J=1.2, 7.8 Hz, 1H), 8.23 (dd, J=1.8, 7.5Hz, 1H), 7.94-7.81 (m, 2H), 3.50 (s, 3H) |
| Chen-3 | 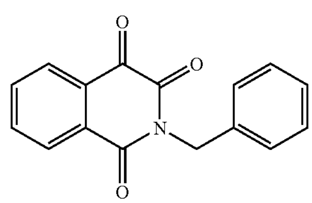 | δ(CDCl$_3$ 300MHz) 8.34 (d, J=7.5 Hz, 1H), 8.19 (d, J=7.5 Hz, 1H), 7.89 (dd, J=6.9, 7.5 Hz, 1H), 7.81 (dd, J=6.9, 7.5 Hz, 1H), 7.51-7.48 (m, 2H), 7.32-7.26 (m, 3H), 5.23 (s, 2H) |
| Chen-4 | 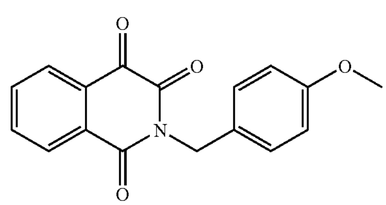 | δ(CDCl$_3$ 300MHz) 8.34 (dd, J=1.2, 7.8 Hz, 1H), 8.19 (dd, J=1.4, 7.8 Hz, 1H), 7.89 (ddd, J=1.2, 7.5, 7.8 Hz, 1H), 7.81 (ddd, J=1.4, 7.5, 7.8 Hz, 1H), 7.47 (d, J=8.6 Hz, 2H), 6.83 (d, J=8.6 Hz, 2H), 5.17 (s, 2H), 3.76 (s, 3H) |

-continued

| Compound number | Chemical structure | ¹H-NMR |
|---|---|---|
| Chen-5 | 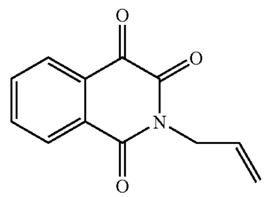 | δ(CDCl₃ 300MHz) 8.35 (dd, J=1.2, 7.5 Hz, 1H), 8.22 (dd, J=1.5, 7.5 Hz, 1H), 7.94-7.81 (m, 2H), 5.96-5.86 (m, 1H), 5.37-5.22 (m, 2H), 4.66 (d, J=7.5 Hz, 2H) |
| Chen-6 | 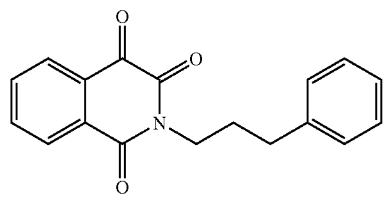 | δ(CDCl₃ 300MHz) 8.30 (d, J=7.8 Hz, 1H), 8.16 (d, J=7.5 Hz, 1H), 7.88-7.80 (m, 2H), 7.23-7.09 (m, 5H), 4.11 (t, J=7.2 Hz, 2H), 2.72 (t, J=7.6 Hz, 2H), 2.10-2.00 (m, 2H) |
| Chen-7 | 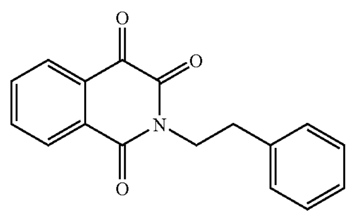 | δ(CDCl₃ 300MHz) 8.33 (dd, J=1.3, 8.0 Hz, 1H), 8.20 (dd, J=1.4, 7.5 Hz, 1H), 7.90 (ddd, J=1.4, 7.2, 8.0 Hz, 1H), 7.83 (ddd, J=1.3, 7.2, 7.5 Hz, 1H), 7.35-7.18 (m, 5H), 4.26 (t, J=8.4 Hz, 2H), 2.96 (t, J=8.4 Hz, 2H) |
| Chen-8 | 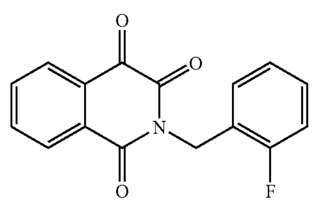 | δ(CDCl₃ 300MHz) 8.36 (dd, J=0.9, 6.6 Hz, 1H), 7.94-7.82 (m, 2H), 7.34-7.31 (m, 1H), 7.26-7.21 (m, 1H), 7.09-7.04 (m, 2H) 5.34 (s, 2H) |
| Chen-9 | 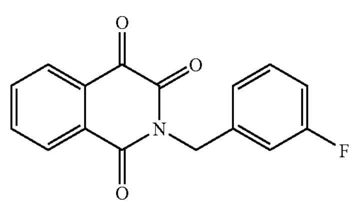 | δ(CDCl₃ 300MHz) 8.36 (dd, J=1.2, 7.8 Hz, 1H), 8.12 (dd, J=1.0, 7.5 Hz, 1H), 7.91 (ddd, J=1.2, 7.5, 7.5 Hz, 1H), 7.84 (ddd, J=1.0, 7.5, 7.8 Hz, 1H), 7.29-7.26 (m, 2H), 7.21-7.19 (m, 1H), 6.97-6.96 (m, 1H), 5.22 (s, 2H) |
| Chen-10 | 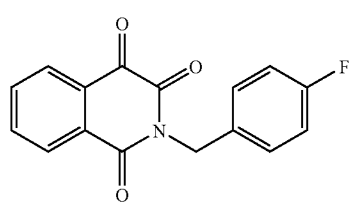 | δ(CDCl₃ 300MHz) 8.34 (dd, J=1.2, 7.8 Hz, 1H), 8.20 (dd, J=1.2, 7.2 Hz, 1H), 7.90 (ddd, J=1.2, 7.3, 7.8 Hz, 1H), 7.82 (ddd, J=1.2, 7.3, 7.8 Hz, 1H), 7.48 (ddd, J=2.3, 5.4, 8.5 Hz, 2H), 7.00 (ddd, J=2.3, 5.4, 8.5 Hz, 2H), 5.19 (s, 2H) |
| Chen-11 | 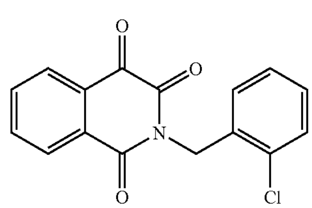 | δ(CDCl₃ 300MHz) 8.36 (dd, J=1.2, 7.2 Hz, 1H), 8.26 (dd, J=1.2, 7.5 Hz, 1H), 7.95-7.84 (m, 2H), 7.39 (dd, J=1.8, 7.5 Hz, 1H), 7.21-7.11 (m, 3H), 5.37 (s, 2H) |

-continued

| Compound number | Chemical structure | $^1$H-NMR |
|---|---|---|
| Chen-12 | 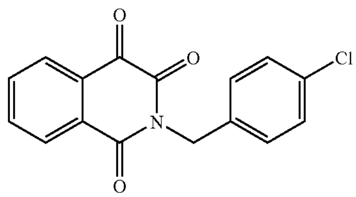 | δ(CDCl$_3$ 300MHz) 8.34 (dd, J=1.5, 7.5 Hz, 1H), 8.20 (dd, J=1.5, 7.5 Hz, 1H), 7.90 (ddd, J=1.5, 7.5, 7.5 Hz, 1H), 7.82 (ddd, J=1.5, 7.5, 7.5 Hz, 1H), 7.45 (dd, J=2.0, 6.9 Hz, 2H), 7.26 (dd, J=2.0, 6.9 Hz, 2H), 5.19 (s, 2H) |
| Chen-13 | R$_1$ = NO$_2$, R$_2$ = H<br>R$_1$ = H, R$_2$ = NO$_2$ | δ(DMSO 300MHz) 12.24 (br, 1H), 12.23 (br, 1H), 8.69 (d, J=2.4 Hz, 1H), 8.65 (d, J=2.7 Hz, 1H), 8.61 (dd, J=2.7, 8.3 Hz, 1H), 8.60 (dd, J=2.4, 8.7 Hz, 1H), 8.36 (d, J=8.3 Hz, 1H), 8.26 (d, J=8.7 Hz, 1H) |
| Chen-14 | 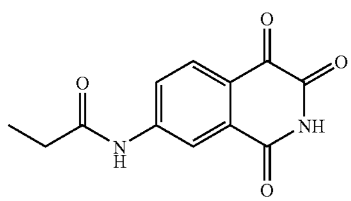 | δ(CD$_3$COCD$_3$, 300MHz) 10.86 (br, 1H), 9.79 (br, 1H), 8.56 (d, J=1.8 Hz, 1H), 8.15 (dd, 1.8, 8.3 Hz, 1H), 8.09 (d, J=8.3 Hz, 1H), 2.50 (q, J=7.5 Hz, 2H) 1.17 (t, J=7.5 Hz, 3H) |
| Chen-15 | 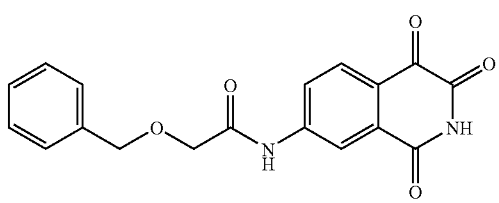 | δ(DMSO 300MHz) 11.96 (br, 1H), 10.53 (br, 1H), 8.50 (d, J=2.0 Hz, 1H), 8.09 (dd, J=2.0, 8.6 Hz, 1H), 8.03 (d, J=8.6 Hz, 1H), 7.43-7.31 (m, 5H), 4.64 (s, 2H), 4.19 (s, 2H) |
| Chen-16 | 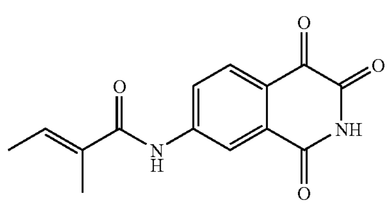 | δ(CDCl$_3$ 300MHz) 8.66 (br, 1H), 8.34 (dd, J=2.3, 8.6 Hz, 1H), 8.249 (d, J=2.3 Hz, 2H), 8.248 (d, J=8.6 Hz, 1H), 7.88 (br, 1H), 6.66-6.63 (m, 1H), 2.04 (s, 3H), 1.88 (d, J=6.9 Hz, 3H) |
| Chen-17 | 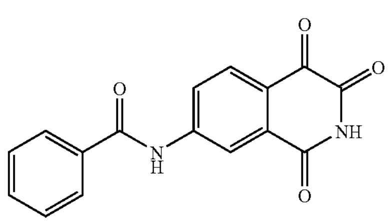 | δ(CD$_3$COCD$_3$ 300MHz) 10.89 (br, 1H), 10.19 (br, 1H), 8.76 (d, J=2.3 Hz, 1H), 8.43 (dd, J=2.3, 8.8 Hz, 1H), 8.18 (d, J=8.8 Hz, 1H), 8.10-8.07 (m, 2H), 7.67-7.62 (m, 1H), 7.59-7.54 (m, 2H) |
| Chen-18 | 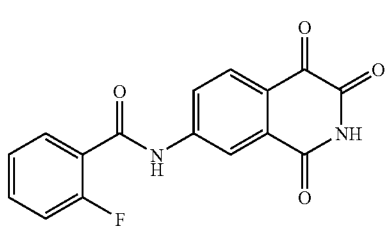 | δ(DMSO 300MHz) 11.99 (br, 1H), 11.10 (br, 1H), 8.57 (d, J=2.1 Hz, 1H), 8.14 (dd, J=2.1, 8.7 Hz, 1H), 8.08 (d, J=8.7 Hz, 1H), 7.77-7.71 (m, 1H), 7.66-7.61 (m, 1H), 7.43-7.35 (m, 1H) |

-continued

| Compound number | Chemical structure | ¹H-NMR |
|---|---|---|
| Chen-19 | 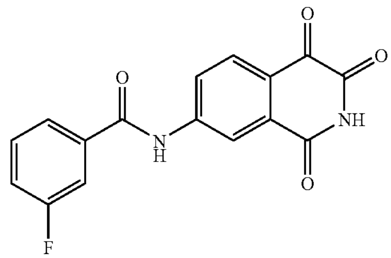 | δ(CD₃COCD₃, 300MHz) 10.90 (br, 1H), 10.22 (br, 1H), 8.74 (d, J=1.8 Hz, 1H), 8.42 (dd, J=1.8, 8.4 Hz, 1H), 8.19 (d, J=8.4 Hz, 1H), 7.94 (d, J=8.1 Hz, 1H), 7.84 (d, J=9.6 Hz, 1H), 7.63 (dd, J=8.1, 13.8 Hz, 1H) |
| Chen-20 | 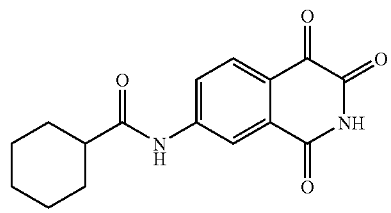 | δ(CD₃COCD₃, 300MHz) 10.84 (br, 1H), 9.71 (br, 1H), 8.57 (d, J=2.2 Hz, 1H), 8.19 (dd, J=2.2, 8.7 Hz, 1H), 8.10 (d, J=8.7 Hz, 1H), 2.51-2.41 (m, 1H), 1.96-1.91 (m, 2H), 1.87-1.79 (m, 2H), 1.70-1.66 (m, 1H), 1.59-1.47 (m, 2H), 1.39-1.35 (m, 1H), 1.30-1.23 (m, 2H) |
| Chen-21 | 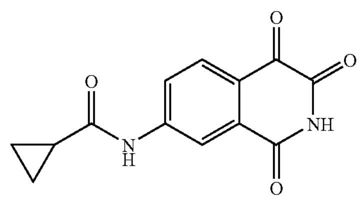 | δ(DMSO 300MHz) 11.95 (br, 1H), 10.91 (br, 1H), 8.42 (d, J=2.1 Hz, 1H), 8.02 (br, 2H), 1.84 (m, 1H), 0.89 (m, 4H) |
| Chen-22 | 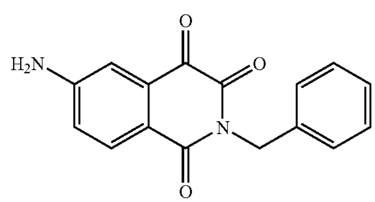 | δ(CDCl₃ 300MHz) 8.11 (d, J=8.7 Hz, 1H), 7.49 (d, J=6.6 Hz, 2H), 7.31-7.30 (m, 3H), 7.28 (s, 1H), 7.01 (dd, J=2.4 Hz, 1H), 5.20 (s, 2H), 4.42 (br, 2H) |
| Chen-23 | 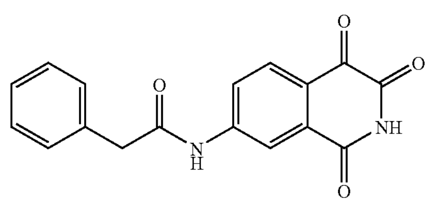 | δ(CDCl₃ 300MHz) 8.65 (br, 1H), 8.25 (dd, J=2.0, 8.3 Hz, 1H), 8.20 (d, J=8.3 Hz, 1H), 8.05 (d, J=2.0 Hz, 1H), 7.57 (br, 1H), 7.48-7.40 (m, 3H), 7.36-7.31 (m, 2H), 3.83 (s, 2H) |
| Chen-24 | 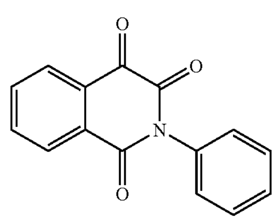 | δ(CDCl₃ 300MHz) 8.40 (dd, J=1.2, 7.1 Hz, 1H), 8.31 (dd, J=1.5, 7.3 Hz, 1H), 7.96 (ddd, J=1.5, 7.8 Hz, 1H), 7.90 (ddd, J=1.2, 7.3 Hz, 1H), 7.58-7.50 (m, 3H), 7.27-7.24 (m, 2H) |
| Chen-25 | 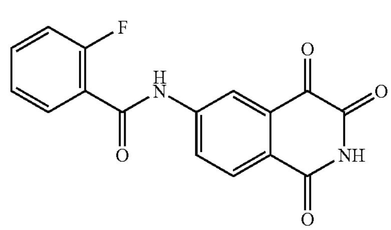 | δ(DMSO 300MHz) 11.89 (br, 1H), 11.02 (br, 1H), 8.47 (d, J=2.4 Hz, 1H), 8.17 (dd, J=2.4, 8.4 Hz, 1H), 8.13 (d, J=8.4 Hz, 1H), 7.76-7.71 (m, 1H), 7.66-7.60 (m, 1H), 7.43-7.33 (m, 2H) |

-continued

| Compound number | Chemical structure | $^1$H-NMR |
|---|---|---|
| Chen-26 | 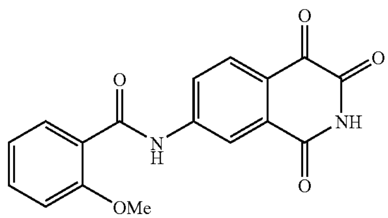 | δ(DMSO 300MHz) 11.97 (br, 1H), 10.76 (br, 1H), 8.59 (d, J=2.1 Hz, 1H), 8.14 (dd, J=2.1, 8.4 Hz, 1H), 8.06 (d, J=8.4 Hz, 1H), 7.63 (dd, J=2.1, 7.5 Hz, 1H), 7.58-7.52 (m, 1H), 7.21 (d, J=8.4 Hz, 1H), 7.09 (dd, J=7.5, 7.5 Hz, 1H), 3.90 (s, 3H) |
| Chen-27 | 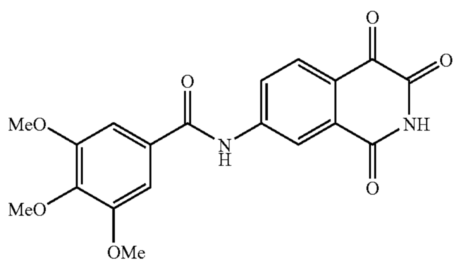 | δ(DMSO 300MHz) 11.98 (br, 1H), 10.70 (br, 1H), 8.56 (d, J=2.0 Hz, 1H), 8.31 (dd, J=2.0, 8.5 Hz, 1H), 8.09 (d, J=8.5 Hz, 1H), 7.35 (s, 2H), 3.89 (s, 6H), 3.75 (s, 3H) |
| Chen-28 | 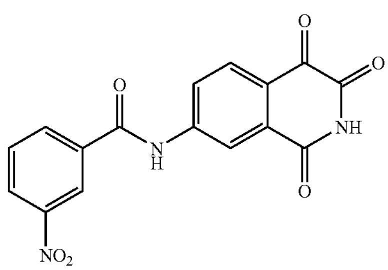 | δ(DMSO 300MHz) 11.98 (br, 1H), 11.17 (br, 1H), 8.87 (dd, J=1.8, 2.4 Hz, 1H), 8.62 (d, J=2.0 Hz, 1H), 8.51-8.45 (m, 2H), 8.31 (dd, J=2.0, 8.5 Hz, 1H), 8.11 (d, J=8.5 Hz, 1H), 7.89 (dd, J=2.1, 2.1 Hz, 1H) |
| Chen-29 | 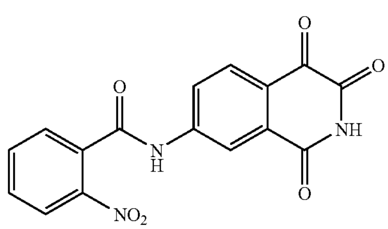 | δ(DMSO 300MHz) 12.00 (br, 1H), 11.33 (br, 1H), 8.52 (d, J=2.0 Hz, 1H), 8.21 (d, J=8.1 Hz, 1H), 8.09 (d, J=8.4 Hz, 1H), 8.04 (dd, J=2.0, 8.4 Hz, 1H), 7.95-7.90 (m, 1H), 7.86-7.79 (m, 2H) |
| Chen-30 | 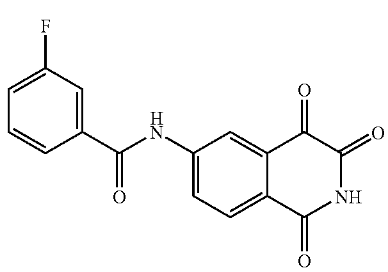 | δ(DMSO 300MHz) 11.88 (br, 1H), 10.85 (br, 1H), 8.52 (d, J=2.0 Hz, 1H), 8.30 (dd, J=2.0, 8.5 Hz, 1H), 8.14 (d, J=8.5 Hz, 1H), 7.87 (d, J=8.4 Hz, 1H), 7.82-7.78 (m, 1H), 7.67-7.48 (m, 2H) |
| Chen-31 | 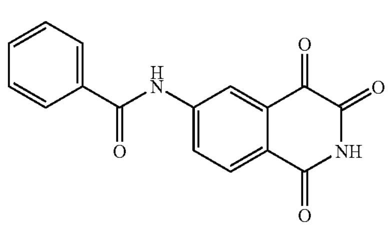 | δ(DMSO 300MHz) 11.87 (br, 1H), 10.81 (br, 1H), 8.55 (d, J=2.1 Hz, 1H), 8.31 (dd, J=2.1, 8.4 Hz, 1H), 8.13 (d, J=8.4 Hz, 1H), 8.03-7.93 (m, 2H), 7.65-7.48 (m, 3H) |

| Compound number | Chemical structure | $^1$H-NMR |
|---|---|---|
| Chen-32 | (4-fluorobenzamide linked to isoquinoline-1,3,4-trione) | δ(DMSO 300MHz) 12.23 (br, 1H), 8.64 (dd, J=2.4, 8.7 Hz, 1H), 8.60 (d, J=2.4 Hz, 1H), 8.35 (d, J=8.7 Hz, 1H), 8.02-7.98 (m, 2H), 7.35-7.29 (m, 3H) |
| Chen-33 | (3-nitrobenzamide linked to isoquinoline-1,3,4-trione) | δ(DMSO 300MHz) 11.90 (br, 1H), 11.11 (br, 1H), 8.86 (m, 1H), 8.53 (d, J=2.4 Hz, 1H), 8.50-8.45 (m, 2H), 8.33 (dd, J=2.4, 8.4 Hz, 1H), 8.16 (d, J=8.4 Hz, 1H), 7.91-7.86 (m, 1H) |
| Chen-34 | (2-methoxyphenylurea linked to isoquinoline-1,3,4-trione) | δ(DMSO 300MHz) 11.80 (br, 1H), 10.00 (br, 1H), 8.38 (br, 1H), 8.28 (d, J=2.4 Hz, 1H), 8.13 (dd, J=1.5, 8.1 Hz, 1H), 8.05 (d, J=8.4 Hz, 1H), 7.78 (dd, J=2.4, 8.4 Hz, 1H), 7.07-6.90 (m, 3H), 3.89 (s, 3H) |
| Chen-35 | (4-nitrophenylacetamide linked to isoquinoline-1,3,4-trione) | δ(DMSO 300MHz) δ(DMSO 300MHz) 11.86 (br, 1H), 10.89 (br, 1H), 8.33 (d, J=2.1 Hz, 1H), 8.22 (d, J=9.0 Hz, 2H), 8.08 (d, J=8.4 Hz, 2H), 8.02 (dd, J=2.1, 8.4 Hz, 1H), 7.63 (d, J=9.0 Hz, 2H), 3.93 (s, 2H) |
| Chen-36 | (phenylurea linked to isoquinoline-1,3,4-trione) | δ(DMSO 300MHz) 11.80 (br, 1H), 9.41 (br, 1H), 8.90 (br, 1H), 8.26 (d, J=2.1 Hz, 1H), 8.04 (d, J=8.5 Hz, 1H), 7.83 (dd, J=2.1, 8.5 Hz, 1H), 7.49 (d, J=7.5 Hz, 1H), 7.31 (dd, J=7.5, 7.5 Hz, 1H), 7.02 (dd, J=7.5, 7.5 Hz, 1H) |
| Chen-37 | (CbzHN- linked to isoquinoline-1,3,4-trione) | δ(DMSO 300MHz) 11.82 (br, 1H), 10.49 (br, 1H), 8.21 (d, J=2.4 Hz, 1H), 8.06 (d, J=8.7 Hz, 1H), 7.90 (dd, J=2.4, 8.7 Hz, 1H), 7.46-7.39 (m, 5H), 5.22 (s, 2H) |
| Chen-38 | (2-nitrobenzamide linked to isoquinoline-1,3,4-trione) | δ(DMSO 300MHz) 11.89 (br, 1H), 11.25 (br, 1H), 8.42 (d, J=1.8 Hz, 1H), 8.21 (d, J=8.1 Hz, 1H), 8.14 (d, J=8.4 Hz, 1H), 8.07 (dd, J=1.8, 8.4 Hz, 1H), 7.95-7.90 (m, 1H), 7.86-7.81 (m, 1H), 7.80-7.77 (m, 1H) |

-continued

| Compound number | Chemical structure | ¹H-NMR |
|---|---|---|
| Chen-39 | 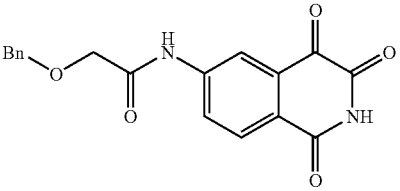 | δ(CDCl₃ 300MHz) 8.72 (br, 1H), 8.54 (br, 1H), 8.38 (dd, J=2.1, 8.7 Hz, 1H), 8.29 (d, J=8.7 Hz, 1H), 8.17 (d, J=2.1 Hz, 1H), 7.43-7.40 (m, 5H), 4.69 (s, 2H), 4.35 (s, 2H) |
| Chen-40 | 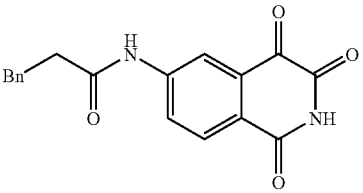 | δ(DMSO 300MHz) 11.85 (br, 1H), 10.52 (br, 1H), 8.33 (d, J=2.4 Hz, 1H), 8.07 (d, J=8.7 Hz, 1H), 8.00 (dd, J=2.1, 8.7 Hz, 1H), 7.29-7.24 (m, 5H), 2.94 (t, J=7.5 Hz, 2H), 2.71 (t, J=7.5 Hz, 2H) |
| Chen-41 | 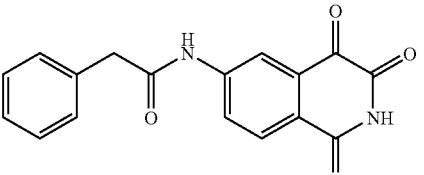 | δ(DMSO 300MHz) 11.83 (br, 1H), 10.77 (br, 1H), 8.34 (d, J=1.8 Hz, 1H), 8.06 (d, J=8.4 Hz, 1H), 8.03 (dd, J=1.8, 8.4 Hz, 1H), 7.35-7.24 (m, 5H), 3.72 (s, 2H) |
| Chen-42 | 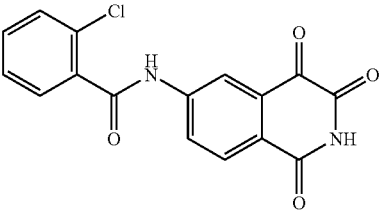 | δ(DMSO 300MHz) 11.89 (br, 1H), 11.12 (br, 1H), 8.48 (s, 1H), 8.13 (br, 2H), 7.68-7.39 (m, 4H) |
| Chen-43 | 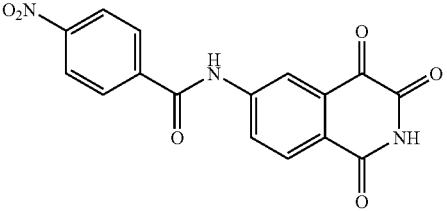 | δ(DMSO 300MHz) 11.89 (br, 1H), 11.09 (br, 1H), 8.53 (d, J=2.1 Hz, 1H), 8.41 (d, J=9.0 Hz, 2H), 8.30 (dd, J=2.1, 8.4 Hz, 1H), 8.25 (d, J=9.0 Hz, 2H), 8.16 (d, J=8.4 Hz, 2H) |
| Chen-44 | 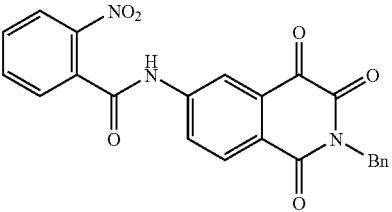 | δ(DMSO 300MHz) 11.30 (br, 1H), 8.48 (d, J=1.8 Hz, 1H), 8.22 (d, J=8.4 Hz, 1H), 8.09 (dd, J=1.8, 8.4 Hz, 1H), 7.96-7.89 (m, 4H), 7.43-7.41 (m, 2H), 7.34-7.23 (m, 3H), 5.09 (s, 2H) |
| Chen-45 | 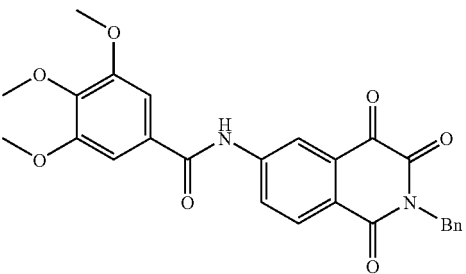 | δ(CDCl₃ 300MHz) 8.46 (dd, J=2.1, 8.7 Hz, 1H), 8.34 (d, J=8.7 Hz, 1H), 8.33 (br, 1H), 8.19 (d, J=2.1 Hz, 1H), 7.52-7.49 (m, 2H), 7.35 (s, 1H), 7.34-7.29 (m, 3H), 7.11 (s, 2H), 5.23 (s, 2H), 3.92 (s, 3H), 3.91 (s, 6H) |

-continued

| Compound number | Chemical structure | ¹H-NMR |
|---|---|---|
| Chen-46 | 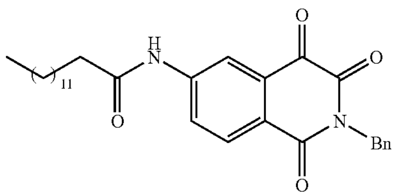 | δ(DMSO 300MHz) 10.50 (br, 1H), 8.38 (d, J=2.1 Hz, 1H), 8.13 (d, J=8.4 Hz, 1H), 8.02 (dd, J=2.1, 8.4 Hz, 1H), 7.40-7.23 (m, 5H), 5.06 (s, 2H), 2.38 (t, J=7.5 Hz, 2H), 1.61 (t, J=6.0 Hz, 2H), 1.23 (br, 20H), 0.85 (t, J=6.6 Hz, 3H) |
| Chen-47 | 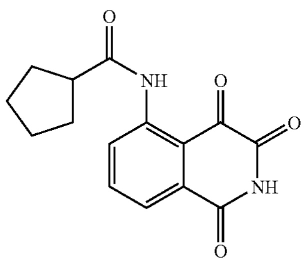 | δ(CDCl₃ 300MHz) 11.63 (br, 1H), 9.22 (dd, J=0.9, 8.4 Hz, 1H), 8.71 (br, 1H), 8.05 (dd, J=0.9, 7.5 Hz, 1H), 7.90 (dd, J=7.5, 8.4 Hz, 1H), 2.93-2.08 (m, 1H), 2.09-1.65 (m, 8H) |
| Chen-48 | 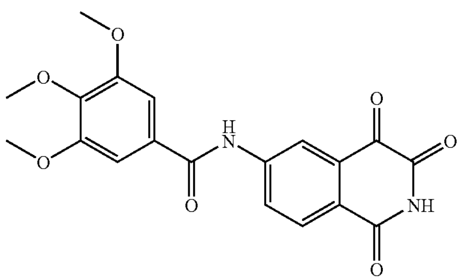 | δ(DMSO 300MHz) 11.88 (br, 1H), 10.65 (br, 1H), 8.47 (d, J=1.8 Hz, 1H), 8.32 (dd, J=1.8, 8.1 Hz, 1H), 8.14 (d, J=8.4 Hz, 1H), 7.34 (s, 2H), 3.89 (s, 6H), 3.75 (s, 3H) |
| Chen-49 | 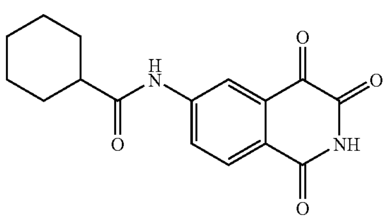 | δ(DMSO 300MHz) 11.84 (br, 1H), 10.45 (br, 1H), 8.35 (d, J=2.1 Hz, 1H), 8.04 (br, 2H), 2.42-2.38 (m, 1H), 1.85-1.14 (m, 10H) |
| Chen-50 | 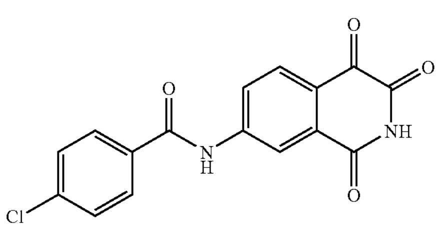 | δ(DMSO 300MHz) 11.99 (br, 1H), 10.93 (br, 1H), 8.61 (d, J=1.5 Hz, 1H), 8.28 (dd, J=1.5, 9.0 Hz, 1H), 8.08 (d, J=9.0 Hz, 1H), 8.05 (d, J=8.7 Hz, 2H), 7.66 (d, J=8.7 Hz, 2H) |
| Chen-51 | 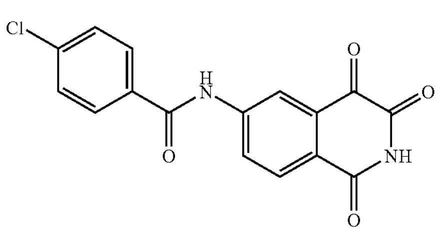 | δ(CDCl₃ 300MHz) 8.08 (br, 2H), 7.64-7.55 (m, 3H), 7.13 (dd, J=7.5, 7.8 Hz, 2H), 6.92 (d, J=7.8 Hz, 2H) |

-continued

| Compound number | Chemical structure | ¹H-NMR |
|---|---|---|
| Chen-52 | 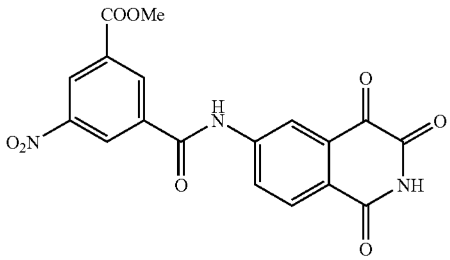 | δ(DMSO 300MHz) 11.91 (br, 1H), 11.25 (br, 1H), 9.09 (dd, J=1.8, 1.8 Hz, 1H), 8.95 (dd, J=1.8, 1.8 Hz, 1H), 8.80 (dd, J=1.8, 1.8 Hz, 1H), 8.51 (d, J=2.1 Hz, 1H), 8.33 (dd, J=2.1, 8.4 Hz, 1H), 8.16 (d, J=8.4 Hz, 1H), 3.99 (s, 3H) |
| Chen-53 | 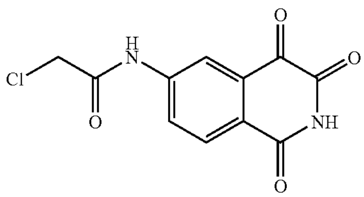 | δ(DMSO 300MHz) 11.88 (br, 1H), 10.91 (br, 1H), 8.33 (d, J=2.1 Hz, 1H), 8.10 (d, J=8.4 Hz, 1H), 8.01 (dd, J=2.1, 8.4 Hz, 1H), 4.35 (s, 2H) |
| Chen-54 | 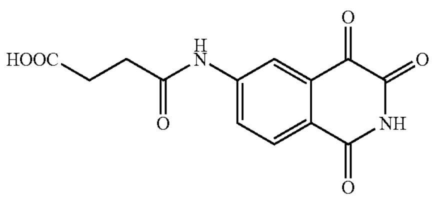 | δ(DMSO 300MHz) 12.11 (br, 1H), 11.84 (br, 1H), 10.60 (br, 1H), 8.34 (d, J=1.8 Hz, 1H), 8.07 (d, J=8.7 Hz, 1H), 7.99 (dd, J=1.8, 8.7 Hz, 1H), 2.64-2.62 (m, 2H), 2.57-2.55 (m, 2H) |
| Chen-55 | 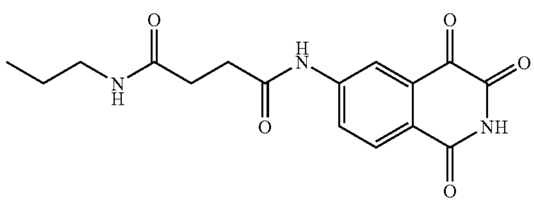 | δ(DMSO 300MHz) 11.83 (br, 1H), 10.57 (br, 1H), 8.35 (d, J=1.8 Hz, 1H), 8.06 (d, J=8.4 Hz, 1H), 7.98 (dd, J=1.8, 8.4 Hz, 1H), 7.88 (t, J=5.1 Hz, 1H), 2.99 (q, J=6.6 Hz, 2H), 2.62 (t, J=6.6 Hz, 2H), 2.43 (t, J=6.6 Hz, 2H), 1.42-1.35 (m, 2H), 0.83 (t, J=7.5 Hz, 3H) |
| Chen-56 | 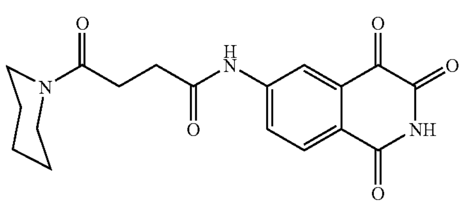 | δ(DMSO 300MHz) 11.82 (br, 1H), 10.57 (br, 1H), 8.35 (d, J=2.1 Hz, 1H), 8.06 (d, J=8.4 Hz, 1H), 7.99 (dd, J=2.1, 8.4 Hz, 1H), 7.80 (d, J=8.4 Hz, 1H), 3.42-3.39 (m, 4H), 2.63 (br, 4H), 1.57-1.51 (m, 4H), 1.40 (br, 2H) |
| Chen-57 | 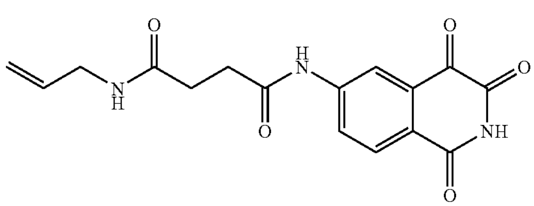 | δ(DMSO 300MHz) 11.83 (br, 1H), 10.57 (br, 1H), 8.35 (d, J=1.8 Hz, 1H), 8.06 (d, J=8.7 Hz, including NH, 2H), 7.98 (dd, J=2.1, 8.7 Hz, 1H), 5.83-5.73 (m, 1H), 5.17-5.02 (m, 2H), 3.69 (t, J=5.4 Hz, 2H), 2.64 (d, J=7.2 Hz, 2H), 2.08 (br, 2H) |
| Chen-58 | 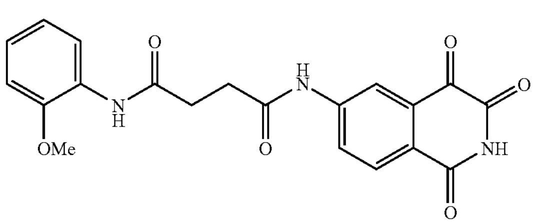 | δ(DMSO 300MHz) 11.82 (br, 1H), 10.60 (br, 1H), 9.18 (br, 1H), 8.36 (d, J=1.8 Hz, 1H), 8.07 (d, J=8.4 Hz, 1H), 8.01 (dd, J=1.8, 8.4 Hz, 1H), 7.94 (d, J=8.1 Hz, 1H), 7.05-7.01 (m, 2H), 6.87 (dd, J=6.0, 6.0 Hz, 1H), 3.83 (s, 3H), 2.75-2.71 (m, 4H) |

-continued

| Compound number | Chemical structure | ¹H-NMR |
|---|---|---|
| Zhang-1 | 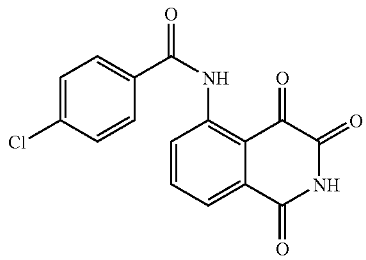 | (DMSO 300MHz) 12.35 (br, 1H), 12.17 (br, 1H), 9.04 (dd, J=1.5, 8.1 Hz, 1H), 8.08 (d, J=6.6 Hz, 2H), 8.02-7.94 (m, 2H), 7.56 (d, J=6.6 Hz, 1H) |
| Zhang-2 | 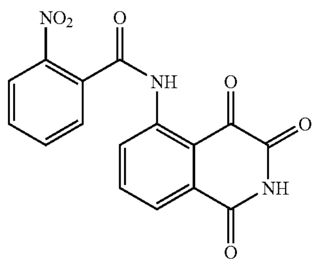 | (DMSO 300MHz) 12.14 (br, 1H), 11.82 (br, 1H), 8.82 (dd, J=3.0, 6.9 Hz, 1H), 8.82 (d, J=8.1 Hz, 1H), 8.03-7.97 (m, 2H), 7.92-7.87 (m, 1H), 7.86-7.82 (m, 1H), 7.80-7.78 (m, 1H) |
| Zhang-3 | 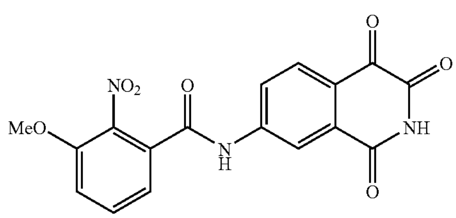 | (DMSO 300MHz) 11.97 (br, 1H), 11.29 (br, 1H), 8.49 (d, J=1.5 Hz, 1H), 8.07-8.05 (m, 2H), 7.72 (t, J=7.8 Hz, 1H), 7.57 (d, J=7.8 Hz, 1H), 7.52 (d, J=7.8 Hz, 1H), 3.90 (s, 3H) |
| Zhang-4 | 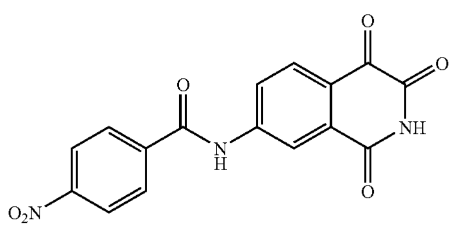 | (DMSO 300MHz) 12.14 (br, 1H), 11.02 (br, 1H), 8.61 (d, J=1.5 Hz, 1H), 8.38 (dd, J=1.5, 8.4 Hz, 1H), 8.32 (d, J=8.7 Hz, 2H), 8.25 (d, J=8.7 Hz, 2H), 8.08 (d, J=8.4 Hz, 1H) |
| Zhang-5 | 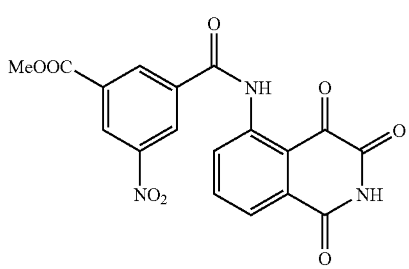 | (DMSO 300MHz) 12.41 (br, 1H), 12.20 (br, 1H), 8.98-8.96 (m, 2H), 8.90 (s, 1H), 8.52 (s, 1H), 8.01-7.98 (m, 2H), 3.99 (s, 3H) |
| Zhang-6 | 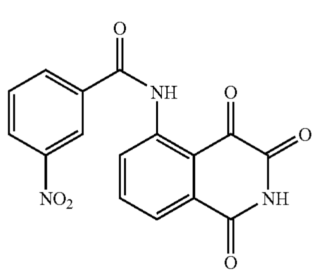 | δ(DMSO 300MHz) 12.42 (br, 1H), 12.19 (br, 1H), 9.01 (dd, J=1.8, 8.1 Hz, 1H), 8.87 (d, J=1.8 Hz, 1H), 8.56 (dd, J=0.9, 7.2 Hz, 1H), 8.45 (dd, J=0.9, 7.2 Hz, 1H), 8.02-7.96 (m, 3H) |

-continued

| Compound number | Chemical structure | ¹H-NMR |
|---|---|---|
| Zhang-7 | 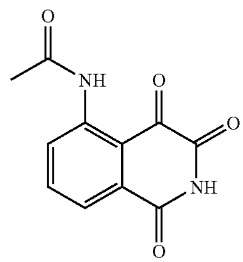 | δ(DMSO 300MHz) 12.10 (br, 1H), 11.34 (br, 1H), 8.84 (d, J=7.5 Hz, 1H), 7.89-7.87 (m, 2H), 2.25 (s, 3H) |
| Zhang-8 | 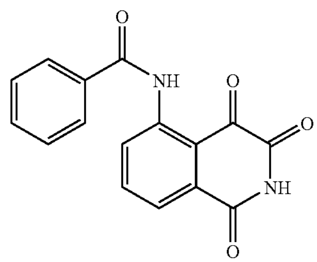 | δ(DMSO 300MHz) 12.40 (br, 1H), 12.16 (br, 1H), 9.08 (dd, J=1.5, 7.8 Hz, 1H), 8.04 (dd, J=1.5, 8.1 Hz, 1H), 7.99-7.92 (m, 3H), 7.69-7.65 (m, 2H), 7.51 (t, J=7.8 Hz, 1H) |
| Zhang-9 | 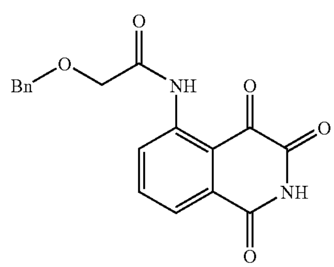 | δ(DMSO 300MHz) 12.19 (br, 1H), 12.09 (br, 1H), 8.99 (dd, J=3.3, 6.3 Hz, 1H), 7.94-7.90 (m, 2H), 7.52 (d, J=7.5 Hz, 2H), 7.40-7.34 (m, 3H), 4.72 (s, 2H), 4.18 (s, 2H) |
| Zhang-10 | 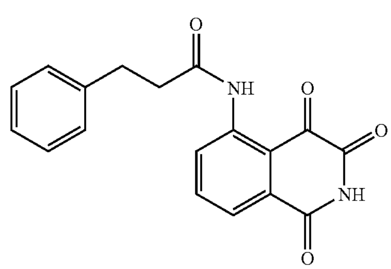 | δ(DMSO 300MHz) 12.09 (br, 1H), 11.41 (br, 1H), 8.85 (dd, J=7.8, 1.8 Hz, 1H), 7.89 (dd, J=7.5, 7.8 Hz, 1H), 7.86 (dd, J=1.8, 7.5 Hz, 1H), 7.29-7.27 (m, 5H), 2.99 (t, J=6.9 Hz, 2H), 2.86 (t, J=6.9 Hz, 2H) |
| Zhang-11 | 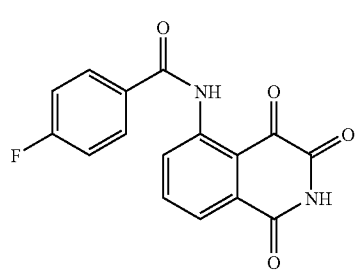 | δ(DMSO 300MHz) 12.35 (br, 1H), 12.17 (br, 1H), 9.04 (d, J=8.1 Hz, 1H), 8.11-8.08 (m, 2H), 7.98-7.94 (m, 2H), 7.52 (t, J=7.8 Hz, 2H) |

-continued
| Compound number | Chemical structure | $^1$H-NMR |
|---|---|---|
| Zhang-12 | 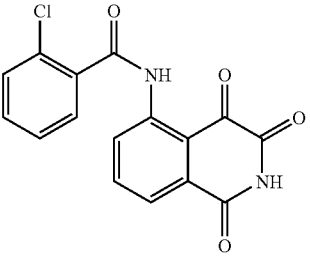 | δ(CDCl$_3$ 300MHz) 12.03 (br, 1H), 9.37 (d, J=8.1 Hz), 9.16 (br, 1H), 8.13 (d, J=7.5 Hz, 1H), 8.01 (dd, J=7.5, 8.1 Hz, 1H), 7.70 (d, J=7.8 Hz, 1H), 7.50-7.40 (m, 3H) |
| Zhang-13 | 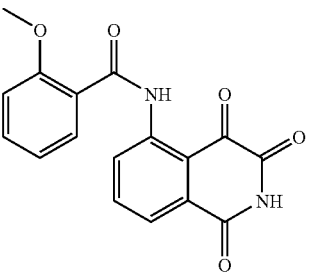 | δ(DMSO 300MHz) 12.72 (br, 1H), 12.10 (br, 1H), 9.18 (dd, J=3.0, 6.3 Hz, 1H), 8.04 (d, J=7.5 Hz, 1H), 8.06-7.92 (m, 2H), 7.66-7.62 (m, 1H), 7.31 (d, J=7.8 Hz, 1H), 7.16 (t, J=7.2 Hz, 1H), 4.10 (s, 3H) |
| Zhang-14 | 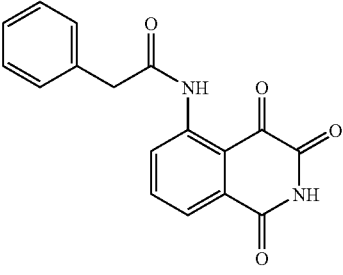 | δ(DMSO 300MHz) 12.05 (br, 1H), 11.39 (br, 1H), 8.87 (d, J=7.8 Hz, 1H), 7.87-7.85 (m, 2H), 7.41-7.32 (m, 5H), 3.88 (s, 2H) |
| Zhang-15 | 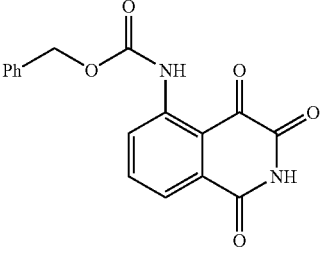 | (DMSO 300MHz) 12.10 (br, 1H), 11.07 (br, 1H), 8.64 (d, J=8.1 Hz, 1H), 7.92 (dd, J=7.2, 8.1 Hz, 1H), 7.83 (d, J=7.2 Hz, 1H), 7.44-7.40 (m, 5H) |
| Zhang-16 | 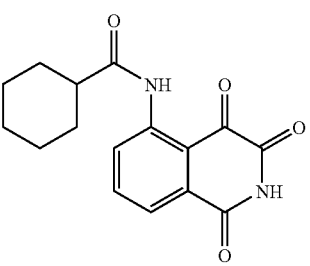 | δ(CDCl$_3$ 300MHz) 11.65 (br, 1H), 9.30 (br, 1H), 9.23 (dd, J=1.2, 8.7 Hz, 1H), 8.06 (dd, J=1.2, 7.5 Hz, 1H), 7.91 (dd, J=7.5, 8.7 Hz, 1H), 2.42-2.28 (m, 1H), 2.09-1.16 (m, 10H) |

| Compound number | Chemical structure | ¹H-NMR |
|---|---|---|
| Zhang-17 | 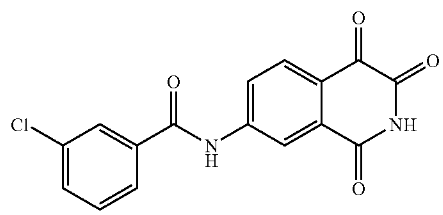 | δ(DMSO 300MHz) 12.00 (br, 1H), 10.85 (br, 1H), 8.60 (d, J=2.1 Hz, 1H), 8.31 (dd, J=8.1, Hz, 1H), 8.06-8.02 (m, 2H), 7.92 (d, J=8.1 Hz, 1H), 7.58-7.46 (m, 2H) |
| Zhang-18 | 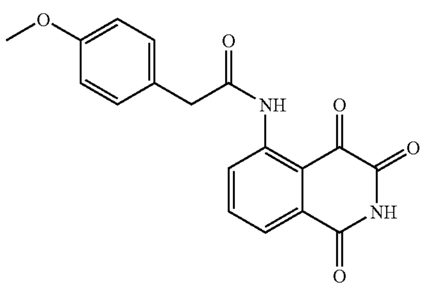 | δ(DMSO 300MHz) 12.04 (br, 1H), 11.36 (br, 1H), 8.88 (dd, J=1.8, 7.8 Hz, 1H), 7.89-7.85 (m, 2H), 7.32 (d, J=8.1 Hz, 2H), 6.95 (d, J=8.1, 2H), 3.76 (s, 2H), 3.70 (s, 3H) |

The teachings of all of the references cited herein are incorporated in their entirety by reference.

What is claimed is:

1. An isoquinoline-1,3,4-trione compound represented having the following structural formula:

wherein, the substituent R₁ is optionally selected from the group consisting of; alkyl; hydroxyl; alkyl substituted by the groups including halogen, alkoxyl or hydroxyl; alkoxyl or alkylamino substituted by the groups including halogen, alkoxyl or hydroxyl; C₂-C₆ alkenyl substituted by oxygen or amine; C₃-C₆ cycloalkyl; substituted aryl; benzyl; alkanoyl; alkanoyl substituted by the groups including halogen, alkoxyl or hydroxyl; C₂-C₆ enoyl; C₃-C₆ cycloalkanoyl; tert-butoxycarbonyl; benzoyl; benzoyl substituted by one, two or three groups including alkylamino; benzylacyl; benzylacyl substituted by one, two or three groups including alkylamino; thienoyl; adamantylcarbonyl; mandeloyl; alkoxyl; alkylamino; cycloalkoxyl; cycloalkylamino; amino; acylamino; alkyloxycarbonyl; cycloalkoxycarbonyl; alkanoyloxy; alkanoylamino; cycloalkyanoyloxy; cycloalkanoylamino; ureido; urenylene; alkanoyl; nitro; carboxyl; and

substituent R₃ is optionally selected from the group consisting of H; alkyl; hydroxyl; alkyl substituted by the groups including halogen, alkoxyl or hydroxyl; alkoxyl or alkylamino substituted by the groups including halogen, alkoxyl or hydroxyl; C₂-C₆ alkenyl substituted by oxygen or amine; C₃-C₆ cycloalkyl; substituted aryl; benzyl; alkanoyl; alkanoyl substituted by the groups including halogen, alkoxyl or hydroxyl; C₂-C₆ enoyl; C₃-C₆ cycloalkanoyl; tert-butoxycarbonyl; benzoyl; benzoyl substituted by one, two or three groups including alkylamino; benzylacryl; benzylacrylcarbonyl substituted by one, two or three groups including alkylamino; thienoyl; adamantylcarbonyl; mandeloyl; alkoxyl; alkylamino; cycloalkoxyl; cycloalkylamino; amino; acylamino; alkyloxycarbonyl; cycloalkoxycarbonyl; alkanoyloxy; alkanoylamino; cycloalkyanoyloxy; cycloalkanoylamino; ureido; urenylene; alkanoyl; nitro; and carboxyl;

Z is CH₂, O or NH;

W is O or H₂;

n=1, 2, 3, 4, or 5.

X is CH₂, NH, O, or S; and

Y is CH, or N.

2. A compound represented having the following structural formula:

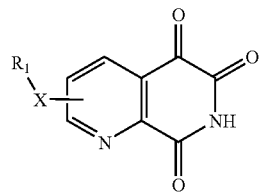

wherein, the substituent R₁ is optionally selected from the group consisting of: H; alkyl; hydroxyl; alkyl substituted by the groups including halogen, alkoxyl or hydroxyl; alkoxyl or alkylamino substituted by the groups including halogen, alkoxyl or hydroxyl; $C_2$-$C_6$ alkenyl substituted by oxygen or amine; $C_3$-$C_6$ cycloalkyl; substituted aryl; or benzyl;

X is $CH_2$, NH, O, or S;

3. The isoquinoline-1,3,4-trione of claim 1, wherein,
when R₁ is alkanoyl; alkanoyl substituted by the groups including halogen, alkoxyl or hydroxyl; $C_2$-$C_6$ enoyl; $C_3$-$C_6$ cycloalkanoyl; tert-butoxycarbanyl; benzoyl; benzoyl substituted by one, two or three groups including alkylamino; benzylacyl; benzylacyl substituted by one, two or three groups including alkylamino; thienoyl; adamantylcarbonyl; or mandeloyl;

X is $CH_2$, NH, O, or S;
Y is CH, or N.

4. The isoquinoline-1,3,4-trione of claim 1, wherein,
when R₁ is alkoxyl; alkylamino; cycloalkoxyl; cycloalkylamino; amino; acylamino; alkyloxycarbonyl; cycloalkoxycarbonyl; alkanoyloxy; alkanoylamino; cycloalkyanoyloxy; cycloalkanoylamino; urcido; urenylene; alkanoyl; nitro; or carboxyl;

X is $CH_2$, NH, O, or S;
Y is CH, or N.

5. A compound of claim 1 selected from the group consisting of

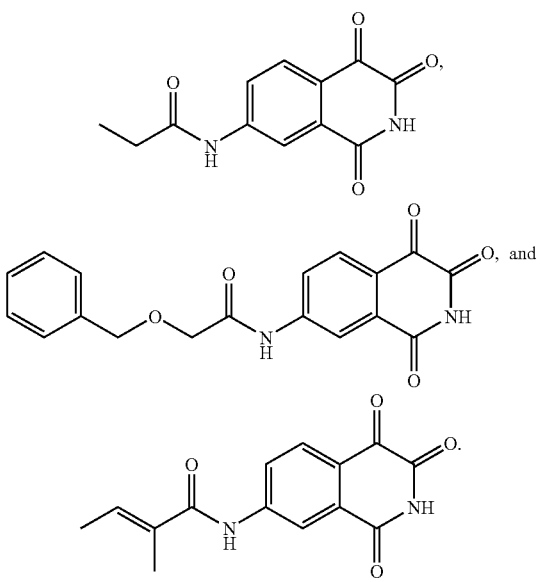

6. A compound of claim 1 selected from the group consisting of

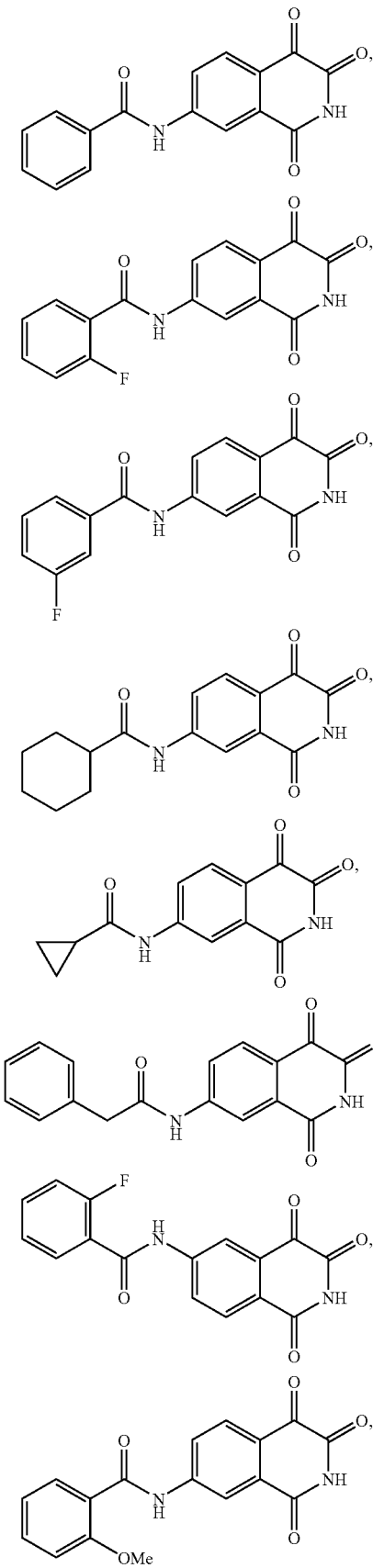

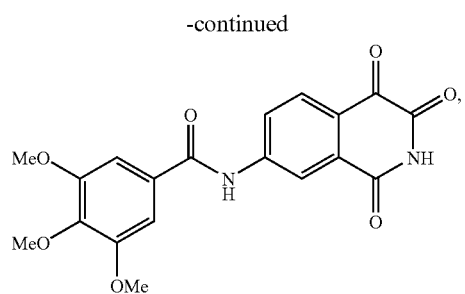
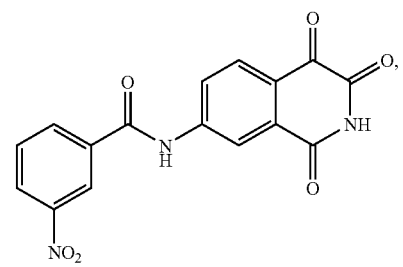
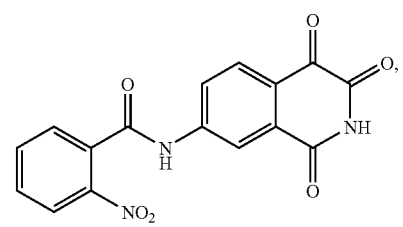
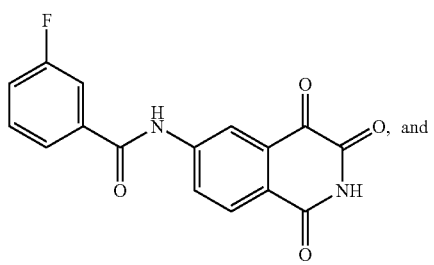
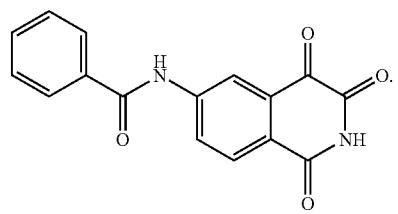
7. A compound of claim 1 selected from the group consisting of
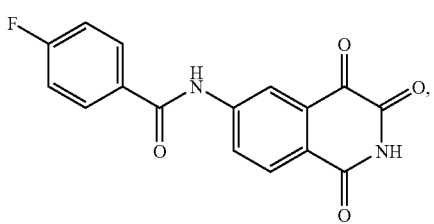
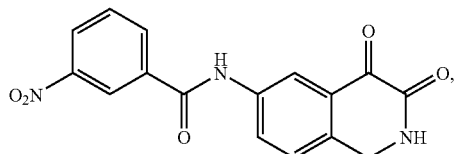
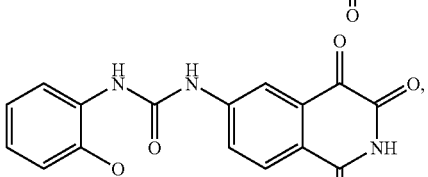
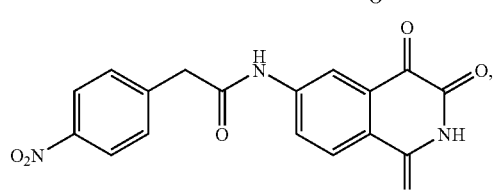
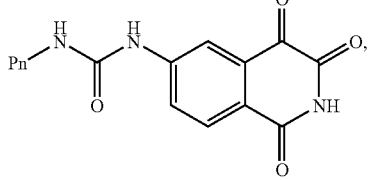
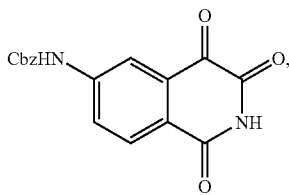
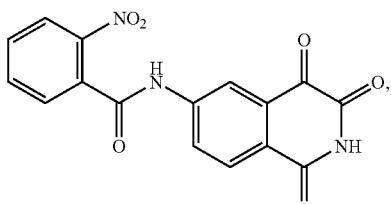
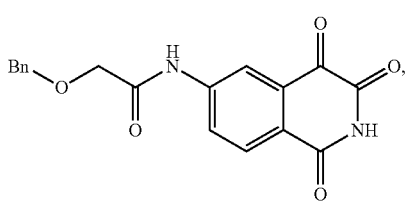
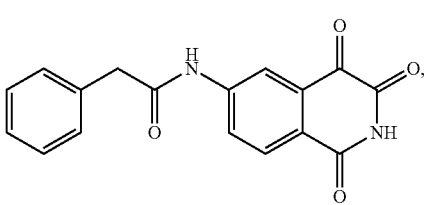

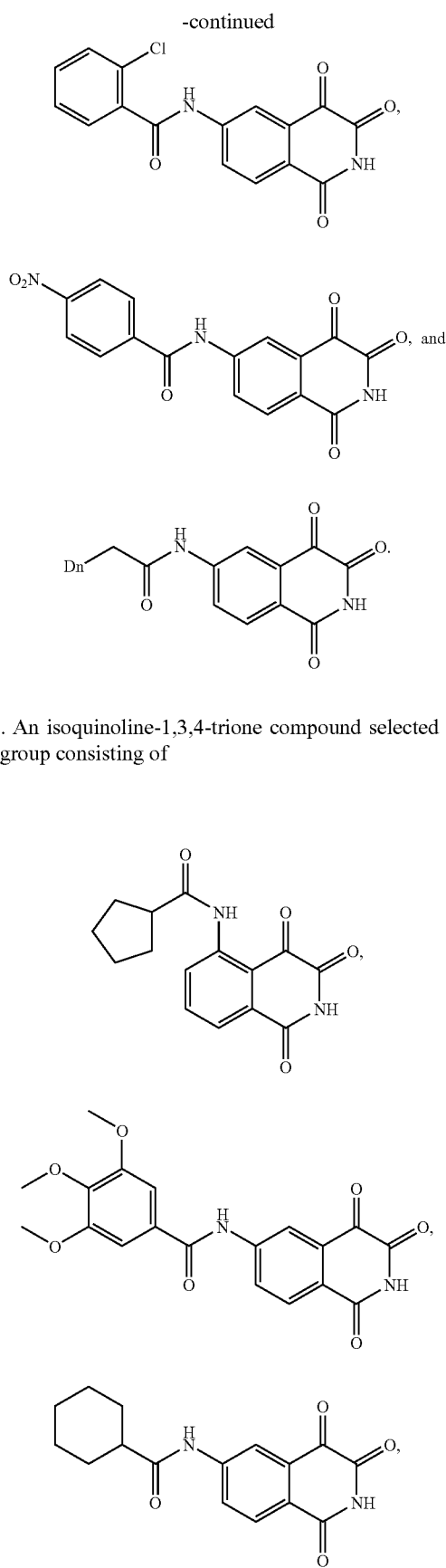
8. An isoquinoline-1,3,4-trione compound selected from the group consisting of
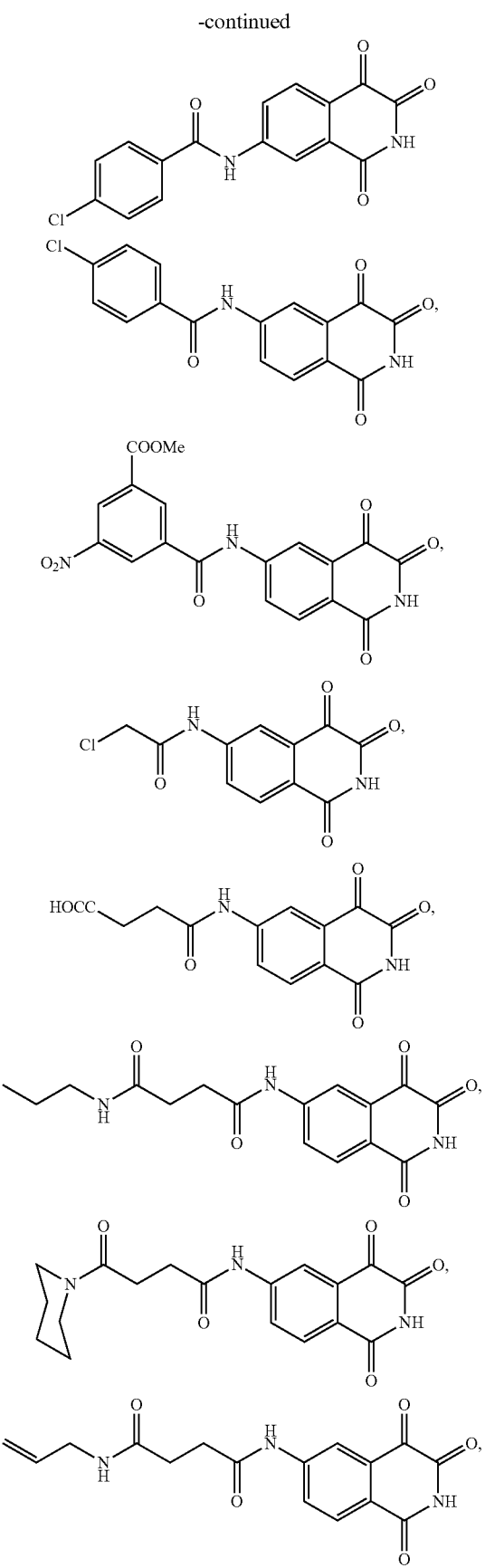

-continued
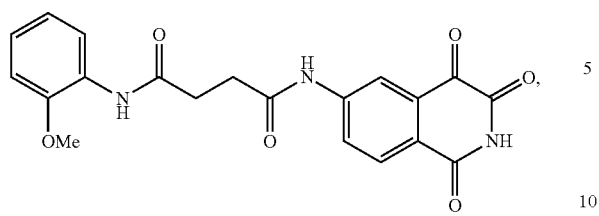
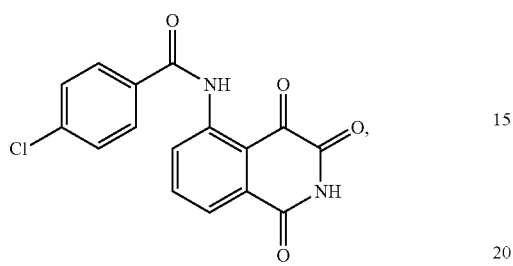
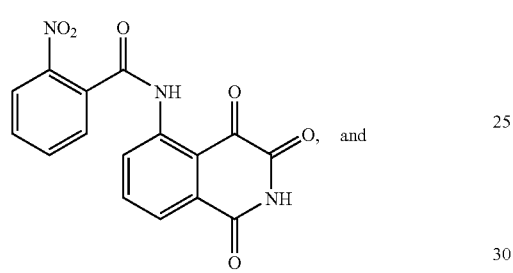
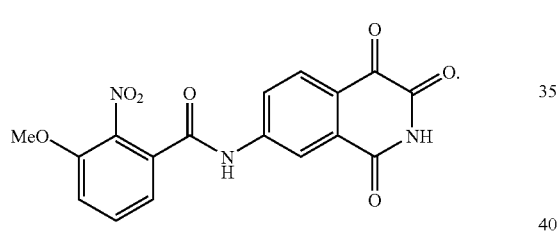
9. A compound of claim 1 selected from the group consisting of
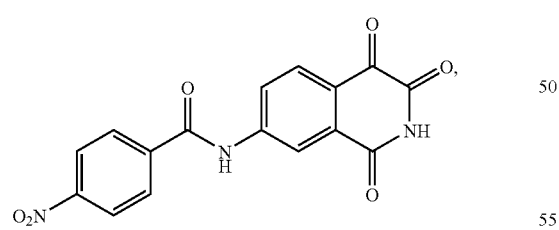
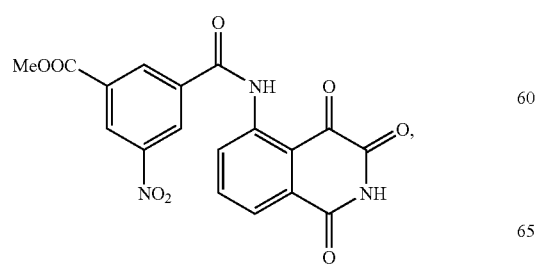
-continued
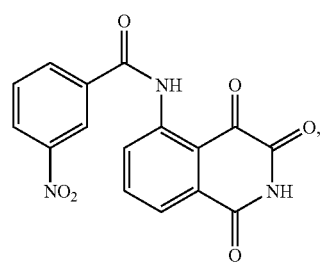
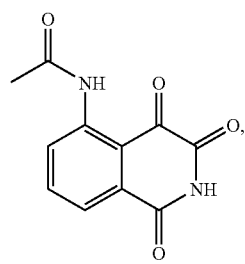
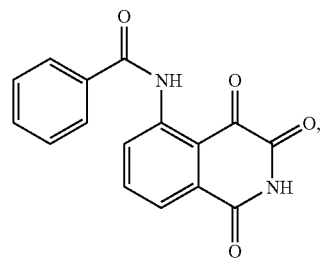
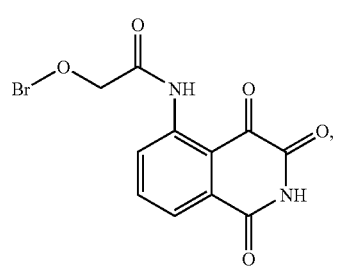
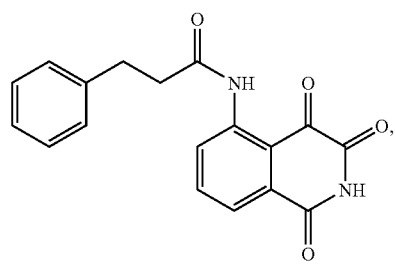
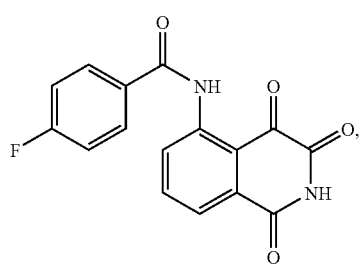

-continued
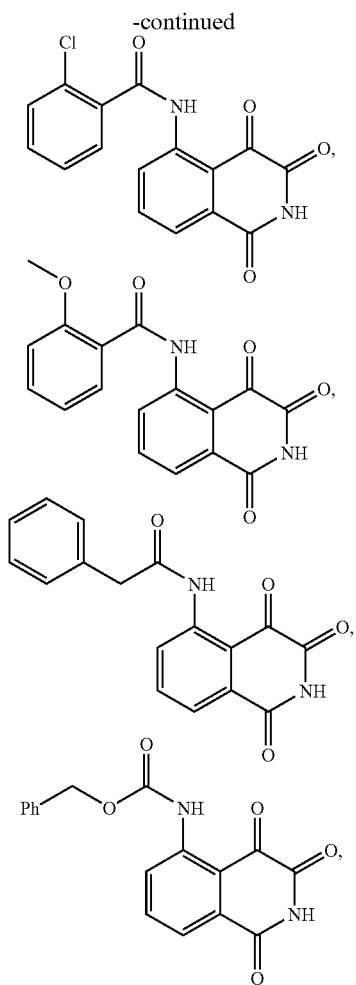
-continued
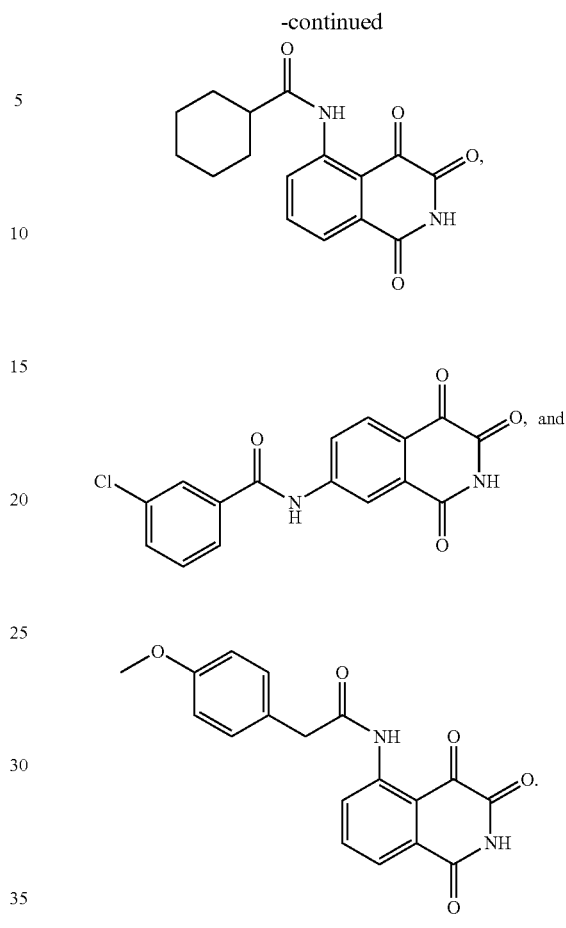
* * * * *